(12) United States Patent
Rao et al.

(10) Patent No.: US 8,465,951 B2
(45) Date of Patent: Jun. 18, 2013

(54) METHOD FOR SIMULTANEOUS DETECTION AND DISCRIMINATION OF BACTERIAL, FUNGAL, PARASITIC AND VIRAL INFECTIONS OF EYE AND CENTRAL NERVOUS SYSTEM

(75) Inventors: Chintalagiri Mohan Rao, Andhra Pradesh (IN); Ikunchala Sridhar Rao, Andhra Pradesh (IN); Puppala Venkat Ramchander, Orissa (IN); Hajib Naraharirao Madhavan, Tamilnadu (IN); Savitri Sharma, Andhra Pradesh (IN); Gita Satpathy, New Delhi (IN); Venkata Banda Ravi Kumar, Bangalore (IN)

(73) Assignee: Council of Scientific & Industrial Research, New Delhi (IN)

( * ) Notice: Subject to any disclaimer, the term of this patent is extended or adjusted under 35 U.S.C. 154(b) by 248 days.

(21) Appl. No.: 12/602,564

(22) PCT Filed: May 27, 2008

(86) PCT No.: PCT/IN2008/000334
§ 371 (c)(1),
(2), (4) Date: Jun. 30, 2010

(87) PCT Pub. No.: WO2008/146306
PCT Pub. Date: Dec. 4, 2008

(65) Prior Publication Data
US 2011/0111969 A1   May 12, 2011

(30) Foreign Application Priority Data
Jun. 1, 2007 (IN) .......................... 1178/DEL/2007

(51) Int. Cl.
*C12P 19/34* (2006.01)
*C07H 21/04* (2006.01)

(52) U.S. Cl.
USPC ..................................... 435/91.2; 536/24.33

(58) Field of Classification Search
None
See application file for complete search history.

(56) References Cited

U.S. PATENT DOCUMENTS

| 2003/0194393 A1 | 10/2003 | Milhausen |
| 2007/0134652 A1* | 6/2007 | Slepnev et al. .................. 435/5 |

FOREIGN PATENT DOCUMENTS

| EP | 1 310 569 A2 | 5/2003 |
| WO | 00/73436 A1 | 12/2000 |
| WO | 2004/099438 A1 | 11/2004 |
| WO | 2006/080501 | 8/2006 |

OTHER PUBLICATIONS

Espacenet English abstract of JP 10-323189 published Dec. 8, 1998.
Espacenet English abstract of CN 1995387 A published Jul. 11, 2007.
Espacenet English abstract of JP 2006-129810 A published May 25, 2006.
Dworkin, Lydia L., et al., "Real-Time Quantitative Polymerase Chain Reaction Diagnosis of Infectious Posterior Uveitis", Archives of Ophthalmology, vol. 120, No. 11, Nov. 1, 2002, pp. 1534-1539.
Suzuki, T., et al., "Application of Multiplex-PCR and DNA-microarray techniques for identifying conjunctivitis-causing pathogens", Investigative Ophthalmology & Visual Science, Association for Research in Vision and Ophthalmology, vol. 45, No. suppl. 1, Apr. 1, 2004, p. 1.
Chichili, G. R., et al., Multiplex polymerase chain reaction for the detection of herpes simplex virus, varicella-zoster virus and cytomegalovirus in ocular specimens, Current Eye Research, vol. 27, No. 2, Jan. 1, 2003, pp. 85-90.
Elnifro, Elfath M., et al., "Multiplex PCT: Optimization and Application in Diagnostic Virology", Clinical Microbiology Reviews, vol. 13, No. 4, Oct. 1, 2000, pp. 559-570.

* cited by examiner

*Primary Examiner* — Teresa E Strzelecka
*Assistant Examiner* — Suchira Pande
(74) *Attorney, Agent, or Firm* — Ladas & Parry LLP

(57) ABSTRACT

The present invention relates to the diagnostic methods for identification of the single causative agent or more than one causative agent of ocular and nervous system infections among many probable pathogens, which can cause the infection. All the pathogens affecting a discrete area of eye or nervous system generally cause same clinical manifestations or syndromes. The present invention relates to detection and discrimination of the pathogen among the set of probable pathogens in a single test without resorting to a battery of tests each being directed at detection of one pathogen. The current invention aims at the syndrome based diagnostic replacing the diagnostics based on detection of individual pathogens.

9 Claims, 3 Drawing Sheets

METHOD FOR SIMULTANEOUS DETECTION AND DISCRIMINATION OF BACTERIAL, FUNGAL, PARASITIC AND VIRAL INFECTIONS OF EYE AND CENTRAL NERVOUS SYSTEM

FIELD OF INVENTION

The present invention relates to the diagnostic methods for identification of the single causative agent or more than one causative agent of ocular and nervous system infections among many probable pathogens, which can cause the infection. All the pathogens affecting a discrete area of eye or nervous system generally cause same clinical manifestations or syndromes. The present invention relates to detection and discrimination of the pathogen among the set of probable pathogens in a single test without resorting to a battery of tests each being directed at detection of one pathogen. The current invention aims at the syndrome based diagnostic replacing the diagnostics based on detection of individual pathogens.

BACKGROUND OF THE INVENTION

Infections of the eye can be clinically classified according to the anatomical compartment harboring and consequently affected by the infection. There are many organisms which can cause ocular infections and are in detail described in "Principles and Practice of Infectious Diseases, 6$^{th}$ Edition, Gerald Mandell et al (Eds) Elsevier Churchill Livingston, pp 1387-1418 (2005) the disclosure of which is incorporated by reference here.

Ophthalmic infections can be classified into the following categories based clinician's initial diagnosis:
1. External ocular Infections such as Keratitis and Conjunctivitis
2. Infectious Endophthalmitis
3. Uveitis
4. Retinitis There are many external ocular infections caused by several bacteria and fungi. The fact that conjunctiva and cornea harbor many non-pathogenic bacteria and fungi as passengers due to the exposure to the environment vitiates detection of specific pathogens (bacteria and fungi) in a scraping or a swab taken from conjunctiva or cornea. In the presence of suppuration or ulceration with pus, clinicians make provisional diagnosis of bacterial infection and treat patients with broad-spectrum antibiotics applied topically. However crucial infections difficult to diagnose but eminently curable are:
  Herpes simplex (causing Keratitis)
  Adenoviral kerato-conjunctivitis (some times caused in epidemic proportions)
  *Chlamydia trachomatis* (causing follicular conjunctivitis leading to trachoma and adult inclusion conjunctivitis)
  Varicella conjunctivitis (also called Herpes zoster conjunctivitis)
  Rapidly growing *Mycobacteria* such as *M. chelonae* and *M. fortuitum* (cause infections after LASIK, a surgery conducted in order to reduce the refractive errors)
  Infectious Endophthalmitis can be caused generally by a
  Gram-positive bacteria
  Gram-negative bacteria
  Anaerobic organisms viz. *Propionibacterium acnes*
  Fungi.

Quite commonly the infection is post operative and spreads very fast resulting in blindness. Most important information required for treatment is whether the causative agent is bacterium or fungus and if it is bacterium whether it is aerobic or anaerobic. Endogenous infections caused by haematogenous spread are rare.

Uveitis is generally caused by
  *Mycobacterium tuberculosis,*
  *M. chelonae,*
  *M. fortuitum,*
  *Toxoplasma gondii*

Retinitis is generally seen in immuno-compromised individuals and is caused by
  Cytomegalovirus
  Herpes simplex virus
  Varicella zoster virus Significant loss of vision occurs in all these patients and early and timely diagnosis of these organisms is an important component in prevention of blindness across the globe. The actual incidence of these infections may be relatively higher in developing nations. Many diagnostic techniques are for the diagnosis of eye infections as detailed in Prior Art.

Central Nervous system infections can be classified in to the following categories:
  Acute Pyogenic Meningitis:
  generally seen in children and is caused by organisms such as
  *Haemophilus influenza,*
  *Neisseria meningitides* and
  *Streptococcus pneumoniae.*

Bacterial cultures or smear microscopy of the Cerebro-Spinal Fluid (CSF) sediments lack sensitivity. An additional complicating factor is that prior treatment of the patient with antibiotics can lead to a false-negative result of both gram-stain and culture from CSF. For these reasons, physicians are hesitant to rely on culture results and will opt to complete a full 10-14 day course of intravenous antibiotics, which in the majority of cases is not necessary. Once partially treated, the cases are indistinguishable from chronic meningitis caused by.
  *Mycobacterium tuberculosis*
  Various fungi
  Viral encephalitis caused by a series of therapeutically amenable viruses viz., HSV, CMV and VZV.

Encephalitis generally caused by a variety of viruses both endemic and epidemic. However, Herpes simplex, Cytomegaloviruses and Varicella zoster are the viruses for which specific antiviral therapy is available. Other treatable encephalitic agent is *Toxoplasma gondii*.

PRIOR ART

The classical method for detecting a pathogen (bacteria, yeast and other fungi, parasites and viruses) in a clinical sample involves culturing of the sample in order to expand the number of pathogens present into observable colony growths, which can then be identified and enumerated by standard laboratory tests. If desired, the cultures can also be subjected to additional testing in order to determine susceptibility of a pathogen to drug treatment. For accurate identification of the infecting species the clinician must rely on culture results which may require anywhere from 3 days (as in the case of most bacteria including rapidly growing mycobacteria) to 8 weeks as in case of *Mycobacterium tuberculosis*. In order to accurately identify the species of bacterium the culture is followed by extensive biochemical testing that may require additional days or even weeks. Most often it is important to make this determination quickly due to the severity of the disease and the necessity of immediate drug intervention. The culture techniques referred to here are mostly useful in diagnosis of bacterial infections and fungal infections and they are not generally employed for diagnostic purposes in case of viral infections especially since the frequency of the isolation of viruses by culturing from a clinical sample is less than 15%.

The appropriate sample for the diagnosis of infections such as eye infections and infections of nervous system is an additional critical issue in success of diagnosis in detection of the aetiological agent of the underlying syndrome such as kerato conjunctivitis, endophthalmitis, uveitis, retinitis, meningitis, and encephalitis. In these cases infection is highly localized and is thus confined to the eye or CNS. Body fluids such as blood, plasma or serum do not contain the infectious agent. External ocular infections require a specimen such as corneal scrapings or conjunctival swab while infectious endophthalmitis requires either vitreous aspirate in ophthalmologist's office or preferably a sample of vitrectomy in which case 20 ml of vitreous wash by Hank's Balanced Salt solution is taken in an operating room. Simple aspirate of vitreous quite often is inadequate to diagnose fungal and bacterial endophthalmitis by smear examination and culture. The preferred sample in case of both uveitis and retinitis is 0.2 to 0.3 mL, of vitreous fluid collected in a 27-gauge needle. The best biological fluid used for diagnosis of central nervous system infections is cerebrospinal fluid. In one embodiment of the current invention, aqueous humor or vitreous fluid in case of endophthalmitis will be sufficient in order to detect and discriminate the infectious agent. This obviates the necessity of surgical procedure such as vitrectomy to be performed in an operating room.

DNA based methods for identification of pathogen offer simple, robust and foolproof alternative to classical methods, which are time consuming and require personnel with specialized training and skills. It is possible to introduce errors that sometimes lead to ambiguous identification of pathogens, and therefore result in a wrong diagnosis/treatment while performing classical methods. DNA based pathogen identification on the other hand, offers advantage to identify the pathogen at a much early stage, sometimes earlier than clinical symptoms are seen (sub-clinical stage). Once the conditions are standardized, pathogen identification is foolproof and can be done by a semi-skilled person. DNA based procedures can also be used for evaluating the outcomes of medical interventions (prognostic values). Screening of clinical samples for human pathogens using a DNA based methods such as PCR offers sensitive and definitive diagnosis and initiation of effective treatment, even from a small volume of clinical sample (aqueous humor, vitreous fluid, tears, saliva, blood, cerebro-spinal fluid, mucosal or epithelial scraping such as corneal scraping, conjunctival swab, tissue specimen etc.,) containing very few (approximately 20-50) pathogenic organisms per sample. The potential benefits of employing the polymerase chain reaction (PCR) technique is to identify of a specific bacterial or viral pathogen in a relatively short period of time. A viable PCR-based assay has the potential to influence the clinician's decisions of how to institute treatment while the patient is still in the emergency room. Since a PCR-based method of detection does not depend, on the presence of viable organisms but instead relies on genetic material, a PCR-based technique is applicable in all patient cases, even when antibiotics were administered prior to drawing the clinical specimen collection. Some difficulties, however, are associated with PCR-based methods, such as false-positive results due to contaminating nucleic acids and inhibition of the PCR reaction due to complex samples. The following PCR assays have been described for the organisms causing eye and CNS infections.

Herpes Simplex 1 & 2:

PCR based DNA detection of HSV had been shown to be 4 to 5 times more sensitive than viral culture and is not sensitive to transport conditions as mentioned in Wald A., et al. "Polymerase chain reaction for detection of Herpes simplex virus (HSV) on mucosal surface: Comparison with HSV isolation in cell culture". J. Inf. Dis. 188: 1345-1351 (2003). PCR was used to detect HSV in ocular specimen such as aqueous humor, corneal scrapings, Lens aspirates, lens capsular material and vitreous fluid and other clinical specimen such as CSF, genital swabs and cervical swabs Madhavan H N et al. "Detection of herpes simplex virus (HSV) using polymerase chain reaction (PCR) in clinical samples: Comparison of PCR with standard laboratory methods for the detection of HSV". J. Clin. Virol. 14:145-151 (1999). Herein a PCR could detect 1 to 3 particles of HSV in a clinical sample. PCR was also effectively used to identify the Herpes virus serotypes combining PCR and Restriction length polymorphisms of the amplicon as mentioned in the publication of one of the inventors the disclosure of which is incorporated by reference Madhavan H N et al. "Phenotypic and Genotypic methods for the detection of herpes simplex virus serotypes". J. Virol. Methods, 108: 97-102 (2003).

Varicella Zoster Virus:

PCR was applied to detect Varicella infections (Burke D G, et al. "Polymerase chain reaction detection and clinical significance of varicella zoster in cerebrospinal fluid in human immunodeficiency virus infected patients". J. Inf. Dis, 176: 1080 (1996)). Detection of both HSV and VZV in central nervous system was also achieved by using PCR (Sauerbrei A and Wutzler P. "Laboratory diagnosis of central nervous system infection caused by herpes viruses". J. Clin. Virol, 25 s45-s51, (2002)) wherein they concluded that PCR is the gold standard for detection of VZV, the disclosure of which is incorporated here by reference.

Cytomegalovirus A:

Commercially available PCR test called COBAS Amplicor CMV Monitor of Roche Molecular diagnostics, Pleasanton, Calif., USA uses 365 base pair region of DNA Polymerase gene of CMV for detection by amplification. Using gene of the immediate early antigen and DNA polymerase many assays have been described in order to detect presence of CMV in various body fluids (Stanier P, et al. "Detection of human cytomegalovirus in peripheral mononuclear cells and urine samples using PCR". Mol. Cell Probes, 6: 51-58 (1992) and Gerna G, et al. "Monitoring human cytomegalovirus infection and gancyclovir treatment in heart transplant recipients by determination of viraemia, antigenemia and DNAemia". J. Inf. Dis., 164, 488-498 (1991)) the disclosure of which is incorporated herein by reference. CMV infections of the patients were also detected by a nested PCR in various samples such as blood, amniotic fluid, Nasal aspirates, bronchio-alveolar lavage, urine, placental material and bronchial aspirates.

Eye infections caused by all three herpes viruses, HSV, VZV and CMV were detected by PCR as described by one of the inventors in a publication disclosure of which is incorporated here by reference Priya K et al. "Association of herpes viruses in aqueous humour of patients with serpigenous choroiditis: a polymerase chain reaction based study". Ocular Immunology and Inflammation 9: 1-9 (2003). Nested PCR was performed to detect VZV in this study in order to obtain necessary sensitivity. However the nested PCR has the attendant problem of introduction of amplicon contamination within the lab as the PCR product of the first round of amplification has to be transferred to a second PCR tube containing a second set of primers amplifying a smaller region of the gene amplified in the first round of PCR.

Detection of *Mycobacterium tuberculosis* by PCR is the scheme of two FDA approved tests. These are The Amplified *Mycobacterium tuberculosis* Direct test Gen-Probe San Diego, USA and Amplicor *M. tuberculosis* test of Roche Diagnostic Systems, Basel, Switzerland. Many other tests have been known in the art. However using PCR ocular tuberculosis was detected by Madhavan H N et al. "Polymerase chain reaction for detection of *Mycobacterium tuberculosis* in epiretinal membrane in Eales". Disease. Invest. Ophthalmol. Vis. Sci. 41: 822-825 (2000).

*Chlamydia trachomatis* detection by nucleic acid amplification has been used in clinical settings and is described in detail in Black C M, "Current methods of laboratory diagnosis of *Chlamydia trachomatis* infection". Clin. Microbiol. Rev. 10: 160-184 (1997). *Chlamydial* conjunctivitis was detected using PCR on conjunctival swabs and as few as 30 organisms were detected in a clinical sample as detailed in Malathi. J et al. "A hospital based study on prevalence of conjunctivitis due to *Chlamydia trachomatis*". Ind. J. Med. Res., 117:71-75 (2003).

Adenovirus conjunctivitis was diagnosed by a nested PCR in conjunctival swabs as described earlier. Dalapathy S et al. "Development and use of nested polymerase chain reaction (PCR) for the detection of Adenoviruses from conjunctivitis specimen". J. Clin. Virol. 11:77-84 (1998).

*Toxoplasma gondii* causes severe encephalitis and uveitis in case of patients with immunodeficiency. Many PCR test protocols have been used to study various body fluids and tissues and all the PCR tests rely on amplification of B1 gene (Danise A, et al. "Use of polymerase chain reaction assays of aqueous humor in diagnosis of in the differential diagnosis of retinitis in patients infected with human immunodeficiency virus". Clin. Infect. Dis 24: 1100-1106 (1997), Montoya. et al. "Use of polymerase chain reaction in diagnosis of ocular toxoplasmosis. Ophthalmology", 106: 1554-1563 (1999).

Infectious endophthalmitis resulting from post operative infection of the eye is investigated using PCR reactions for eubacterial genes and discrimination by probes in to Gram+ve and Gram−ve as disclosed in detail in Anand A R et al. "Use of polymerase chain reaction (PCR) and DNA probe hybridization to determine the gram reaction of the interacting bacterium in the intraocular fluids of patients with endophthalmitis". J. Infection, 41:221-226 (2000). This study could detect as low as six bacteria in a clinical sample. The ocular infections caused by anaerobic organisms such as *Propionibacterium acnes* were detected rapidly using PCR as described in detail in Therese K L et al. "Polymerase chain reaction in the diagnosis of bacterial endophthalmitis", Brit. J. Opthal. 82:1078-1082 (1998). Fungal endophthalmitis could also be diagnosed rapidly using PCR as disclosed in detail in Anand A R et al. "Polymerase chain reaction in the diagnosis of *Asperigillus* endophthalmitis". Ind. S. Med. Res. 114: 133-140 (2001) and Anand A R et al. "Use of polymerase chain reaction in fungal endophthalmitis". Ophthalmology 108: 326-330 (2001). In both these studies ~0.4 pgs of fungal DNA could be detected.

Various PCR assays described here in employ different thermal profiles of the reaction as primer sets and the genes being detected in each individual PCR are different. Moreover, the reagent concentrations of each of PCR described above had been adjusted in order to optimize the PCR for highest sensitivity for that set of reactants described there in. Optimal reaction conditions vary according to the sequence of nucleotide chain being amplified its size and the complexity of the whole target DNA of the organism or pathogen being detected.

There remains a need, however, for a PCR-based assay that can simultaneously detect and discriminate between the pathogens that cause bacterial fungal, parasitic and viral infections of the eye and central nervous system which in addition to being rapid, is not prone to contamination and which has increased sensitivity and specificity over other methods. It should be easy to use in clinical settings where the identification of infections agent within 24 to 48 hours is important to save lives. The critical issues in accurate diagnosis of eye and brain infections can be summarized as:

The infections of eye and brain are highly localized. There is no trace of the causative agent in easily obtainable biological fluids such as blood, serum, plasma, saliva or pus or purulent discharge from an external wound or ulcer.

The putative biomarkers of any acute infection such as C reactive protein are general and are common to all infections afflicting the human body. Thus are non-specific.

In order to identify the specific causative agent a sample from the eye or CSF is required. The obtainable samples are corneal scrapings for corneal infections; conjunctival swab for conjunctivitis; aqueous humor for endophthalmitis; vitreous humor for uveitis and retinitis. In case of brain infection the preferred sample is always CSF. In all these samples there is a limitation of the amount of sample that can be obtained from a patient in a single sitting. Generally you get a few thousand cells and probably two to three milligrams of the sample in a corneal scraping or a swab. Aqueous humor that can be drawn from a patient's eye at any time is about 100 μL while vitrectomy sample can be up to 200 μL. Up to 5 ml of CSF sample can be drawn but the volume of CSF sample required for PCR will be less than 0.5 ml.

Consequent to the limitation of the volume of the sample is the limited number of bacteria/viruses/parasites present in the sample. In addition as such the dose of the infectious agents is less than that of the dosage observed in many other body compartments such as blood.

The total number of infectious particles present in a sample is directly proportional to the success of detection. Below a critical mass, the infectious agents bacteria and fungi fail to grow in culture and are thus difficult to diagnose. Number of viral particles present in an ocular specimen, are generally below the detection limits of fluorescent antibody detection tests as well as viral cultures thus making the sensitivity of the detection to less than 25%. There are no easy detection systems for parasites such as *Toxoplasma gondii* and the number of parasites are also too few for detection. The tests such as IgM or IgG detection for HSV, CMV, VZV, Adenoviruses, *Chlamydia* and *toxoplasma* are very non-specific and are not of diagnostic significance.

Another major difficulty in diagnosis is all the afflictions of the eye described above are of acute nature and require an immediate and accurate diagnosis for institution of appropriate therapy. Delay beyond 48 hours results in blindness in case of infectious endophthalmitis and necrotising retinitis caused by viral infections needs to be treated within 96 hours of the presentation of the first symptom.

Multiplex PCR had also been performed for some of the pathogens in a given clinical situation and the amplified products were identified in by the molecular weight determination by mass spectrometry as detailed in Detection and identification of pathogens by mass spectrometric determination of the base composition of PCR products.

(Ecker, David J.: Griffey Richard 11.: Sampath, Rangarajan; Hofstandler, Steven A.: Meneil, John; Crooke, Stanley T. (USA). U.S. Pat. Appl. Publ. (2004), 168 pp. Cont.-in-part of U.S. Ser. No. 323,233. Application: U.S. 2003-660122 20030911. Priority: U.S. 2001-798007 20010302; U.S. 2002-431319 20021206; U.S. 2002-323233 20021218; U.S. 2002-326051 20021218; U.S. 2002-325526 20021218; U.S. 2002-325527 20021218; U.S. 2003-443443 20030129; U.S. 2003-443788 20030130; U.S. 2003-447529 20030214).

Multiplex PCR assay followed by gel electrophoresis of the product for identification was attempted for infections of central nervous system as described in Read, S J. and Kurtz, J B. "Laboratory diagnosis of common viral infections of the central nervous system by using a single multiplex PCR screening assay". J. Clin. Microbiol. 37: 1352-1355 (1999).

Multiplex PCR followed by microarray to detect the pathogen was described for detection of pathogens causing respiratory illnesses. (Wang D et al. "Microarray based detection and genotyping of viral pathogens". Proc. Nat. Acad. Sci. USA 99: 15687-15692 (2002)). The detection of amplicons was also attempted using colorimetric microtitre plate assay system wherein the amplicon is labeled with digoxigenin 11-dUTP and biotinylated probes are used to capture amplicon on the microtitre plate. The product is revealed using enzyme labeled antidigoxigenin (Smalling T W et al. "Molecular approaches to detecting herpes simplex virus and enteroviruses in the central nervous system". J. Clin. Microbiol. 40:2317-2322 (2002)).

Multiplex PCR assay of three different genes of same organism viz., morphological transforming region II, UL 83 and glycoprotein O genes of cytomegalovirus was tried successfully in order to quantify the virus in clinical samples as detailed in Madhavan H N et al., "Development and application of a novel multiplex polymerase chain reaction for semi-quantitation of human cytomegalovirus in clinical specimen", J Virol Methods. 141:166-72 (2007)

Line probe assay was also used to detect and discriminate the genotypes of papilloma viruses in cervical samples of women after multiplex PCR assay that amplifies L1 region of all 19 high-risk genotypes (Bauer H M et al. "Detection of human papilloma viruses by polymerase chain reaction" U.S. Pat. No. 5,639,871).

The methods such as mass spectrometry are not practicable even in advanced tertiary medical care centers and microarrays detection based on expensive scanners cannot be afforded in clinical settings. A line probe assay is prone for amplicon contamination.

I. DEFINITIONS

"Nucleotide" means a building block of DNA or RNA, consisting of one nitrogenous base, one phosphate molecule, and one sugar molecule (deoxyribose in DNA, ribose in RNA).

"Oligonucleotide" means a short string of nucleotides. Oligonucleotides are often used as probes to find a matching sequence of DNA or RNA and can be labeled with a variety of labels, such as radioisotopes and fluorescent and chemiluminescent moieties.

"Primer" means a short strand of oligonucleotides complementary to a specific target sequence of DNA, which is used to prime DNA synthesis.

"Uniplex" means a PCR-based assay utilizing a single set of primers in each reaction that amplifies a single pathogen specific DNA sequence "Multiplex" means a PCR-based assay utilizing multiple primer sets in a single reaction, where each primer can amplify a single pathogen specific DNA sequence.

The term "probe" refers to the DNA product (amplicon) resulting from a PCR-based amplification of target DNA.

The term "target" refers to the DNA sequence, specific to individual pathogen, that is immobilized on an inert matrix such as nylon.

"Hybridization" refers to the process of joining two complementary strands of DNA to form a double-stranded molecule; more specifically mentioned here is between the 'probe, and the 'target' DNA sequences.

"The term "detection system" as used herein refers to a method that enables visualization of PCR-amplified DNA products. Examples of suitable detection systems include systems that depend on detection of color, radioactivity, fluorescence or chemiluminescence.

'Pan fungal' means a common gene sequence found in all pathogenic fungi such as *Cryptococcus, Candida, Mucormycosis, Asperigillus* and *Rhizopus* etc. and used for identification of any/all of fungal species.

SUMMARY OF THE INVENTION

The invention provides a set of chemically tagged pathogen specific forward and reverse primers that have been uniquely designed to specifically amplify target sequences from a pathogen in a multiplex polymerase chain reaction at denaturation temperature of 95° C., annealing temperature of 58 to 65° C. and extension at 72° C. The invention also provides a set of target DNA sequences derived from the pathogen specific gene that is immobilized on inert support and specifically hybridizes with PCR amplified product obtained using the pathogen specific forward and reverse PCR primers.

The invention provides a rapid assay for the simultaneous detection of the pathogens responsible for infections of the eye and central nervous system for which immunological parameters are not indicative of an active infection but only indicative of exposure to the pathogen and for which classical microbiological assays such as bacterial and fungal cultures are neither sensitive enough to detect the pathogen nor rapid enough to identify the pathogen within 48 hours.

The present invention combines the high sensitivity of PCR assay and the high specificity of identification by hybridization on to a macro-array with the detection of hybridization by color detection methods, the end result of which can be monitored by naked eye. However fluorescent labels such as Quantum Dots, Cy3, Cy5, FITC can also be used and the product could be visualized by fluorescence microscopy.

The invention features a multiplex assay for the simultaneous detection and discrimination of pathogens that cause infections of the eye and CNS comprising:

i) Processing the clinical samples such as corneal scraping or conjunctival swab or aqueous humor or vitreous fluid or vitrectomy lavage collected or cerebrospinal fluid aspirate or pus collected from brain abscess material or a epiretinal membrane from a patient suspected of being afflicted with eye or a CNS infection, to isolate DNA by standard methods.

ii) Amplifying a specific region of DNA from a gene that is specific to each of the pathogens by a single tube PCR technique using labeled amplification primers for each of the pathogens known to cause CNS and eye infections iii) Detection and discrimination of pathogens using a DNA hybridization wherein the immobilized target sequences specific for each of the pathogens are reacted with amplified DNA probes generated from the PCR reaction and monitoring the hybridization by color development using specific set of reagents.

DETAILED DESCRIPTION OF THE INVENTION

Figure 1:
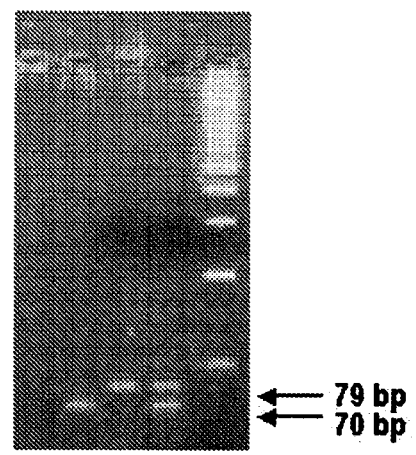
FIG. 1 shows 6% Agarose gel electrophoretogram showing the amplified products of uniplex & multiplex PCR for Hexon gene of Adenovirus & *C. trachomatis* genome.

Design of Unique PCR Primers Suitable for Multiplex PCR of Pathogen(s) DNA from Clinical Sample of Patients Suffering with Eye Infections The following genes from the various known pathogens causing eye infections were chosen based on known information available from the literature.
1. Herpes simplex virus 1 & 2 glycoprotein D
2. Herpes simplex virus 1 & 2 UL 44 gene
3. Herpes simplex virus 1 & 2 DNA polymerase gene
4. Cytomegalovirus Glycoprotein O gene
5. Cytomegalovirus Morphological transformation gene
6. Cytomegalovirus UL 88 gene
7. Varicella zoster ORF 29
8. Varicella zoster DNA polymerase gene
9. Adenoviruses Hexon Gene
10. Eubacterial 16s ribosomal RNA gene I
11. Eubacterial 16s ribosomal RNA gene region II
12. Gram+ve bacterial specific portion of 16s ribosomal RNA gene
13. *Mycobacterium tuberculosis* MPB 64 gene
14. *Mycobacterium fortuitum* 16s-23s RNA gene
15. *Mycobacterium chelonei* 16s-23 s RNA gene
16. *Toxoplasma gondii* B 1 gene
17. *Chlamydia trachomatis* polymorphic protein II
18. Fungal specific portion of 28s ribosomal RNA gene
19. *Propionibacterium acnes* specific portion of 16s-23s ribosomal RNA gene
20. Gram−ve bacterial specific portion of gyr B gene
21. Gram−ve bacterial aconitate hydratase gene
22. Gram−ve ribonuclease 1 gene To further improve certainty of detection of some of the organisms such as Herpes simplex 1 and 2, Cytomegalovirus, Varicella Zoster and Gram-negative bacteria more than one gene of each organism was chosen for amplification purposes. In case of Herpes simplex 1 and 2 and Cytomegalovirus three different genes for each organism were chosen while two genes were chosen for Varicella zoster.

DNA polymerase gene of Herpes viruses is one gene that confers sensitivity to PCR and was used in different studies. In the first study 179 bp product was amplified using thermal cycling conditions of denaturation at 95° C. for 45 sec, annealing at 64° C. for 45 sec and extension at 72° C. for 45 sec. Madhavan H N et al, Detection of herpes simplex virus (HSV) using polymerase chain reaction (PCR) in clinical samples Comparison of PCR with standard laboratory methods for the detection of HSV, J. Olin. Virol. 14:145-151 (1999). While in another study 469 and 391 bp region of the same gene was amplified using different set of primers and thermal cycling conditions of denaturation at 95° C. for 45 sec, annealing at 60° C. for 45 sec and extension at 72° C. for 45 sec. Madhavan H N et al, Phenotypic and Genotypic methods for the detection of herpes simplex virus serotypes. J. Virol. Methods, 108: 97-102. (2003). While detecting different viruses any way different thermal conditions are used as in the case of PCR for HSV, CMV and VZV for identification ocular infections. Priya K et al, Association of herpes viruses in aqueous humour of patients with serpigenous choroiditis: a polymerase chain reaction based study, Ocular Immunology and Inflammation 9:1-9 (2003). In this study the reaction conditions and the concentrations of primers were different for different viruses. It is therefore obvious that it is difficult to design primers and the specific target sequences for a set of known pathogens in order to be able to perform a single tube multiplex PCR reaction that enables a rapid detection and discrimination of one or more pathogen in the given clinical sample.

It was therefore considered necessary to explore the possibility of designing suitable PCR primers and target DNA sequences that are complementary to the product of PCR amplification using known bioinformatic methods.

In order to achieve this objective, the inventors first fixed the following conditions that were preferred for performing multiplex PCR reactions for detection of HSV, CMV and VZV i.e. denaturation at 95° C. followed by annealing at 58° C.-65° C., then followed by extension at 72° C. The optimum temperature of hybridization of the PCR amplified product thus obtained to its specific target DNA sequence for each pathogen immobilized on a solid phase matrix was fixed at 48° C. to 55° C. It was therefore considered necessary to design the set of target DNA sequence for each pathogen in question such that the specific PCR amplified product hybridized to its complementary target DNA sequence at a uniform temperature without resulting in non-specific binding of DNA sequences.

The most difficult element in designing the primers for a multiplex PCR reaction is to design primers in such a way that all of them have same melting temperatures so as to enable amplification of all genes under the same thermal cycling conditions.

The primer sets for amplification were chosen from the above mentioned gene sequences such that all the primers have annealing temperatures in the range of 58-65° C. so that all the 23 genes can be amplified using PCR in the same tube are present invariably in all strains or serotypes of the specific pathogen in question.

Amplicons of different sizes may intereefere with the efficiency of multiplex amplification by PCR method. Therefore the second criterion for choosing primers was fixed as uniform size of amplicon within a range of 66-90 nucleotides All the genes mentioned in the above section were selected for a region containing 66-90 bp length (including of primer sequences).

In order to keep melting temperatures uniform, the primer lengths were varied between 17 to 29 base pairs.

Further, in a multiplex reaction, loop formation in the primers or cross hybridization due to the presence of complementary regions, can interfere with the PCR amplification itself. To avoid all such complications, all the primers were carefully designed to completely eliminate the loop formation or cross hybridization of primers amongst themselves. Care was taken to avoid any non-specific (cross-) amplification by the primer sets i.e. the primers of one organism/gene should not react with the genes of any other organism/gene in the reaction mix.

All the primers are designed in such a way that they match all the nucleotide bases of the pathogen gene in general. However if there is mismatch in some of the strains or species as in the case of primers designed to amplify Gram-positive, gram-negative bacteria and fungi the mismatch is limited to maximum of two nucleotides in the middle of the primer. It was ensured that the 3' end of each primer had always had a perfect match in all the strains of the species being diagnosed.

Criteria described are in addition to the standard criteria described in the art for choosing primer sequences mentioned in detail disclosed here by reference. Molecular cloning: A laboratory manual, Vol 2, Sambrook. J, Russell D W (Eds) Cold Spring Harbor Laboratory Press NY (2001). These criteria being 3' end being G or C avoiding tandem GC repeats and not generally terminating any primer with a T etc.

After design, the primers were used individually and in multiplex format to verify the sensitivity and specificity using standard DNA sequences (genes) of all the pathogens listed. Wherever the sensitivity has fallen short of what was reported in prior art viz., Madhavan H N, et al, Detection of herpes simplex virus (HSV) using polymerase chain reaction (PCR) in clinical samples Comparison of PCR with standard laboratory methods for the detection of HSV, J. Clin. Virol. 14:145-151 (1999); Malathi. J et al. A hospital based study on prevalence of conjunctivitis due to *Chlamydia trachomatis* Ind. J. Medical research, 117:71-75 (2003); Anand A R et al Use of polymerase chain reaction (PCR) and DNA probe hybridization to determine the gram reaction of the interacting bacterium in the intraocular fluids of patients with endophthalmitis. Journal of Infection, 41:221-226 (2000); Anand A R et al. Use of polymerase Chain reaction in fungal endophthalmitis Ophthalmology 108: 326-330 (2001) recognizing a few organisms or viral particles, a different set of primers were selected using the same criterion. Even though some of the primers anneal at 58° C., it was ensured experimentally that all primers gave good amplification at 60° C.

In the present embodiment after a careful evaluation, the following unique primers were selected and used for detection and discrimination of pathogens. These sequences are unique and are not known in the art.

1. Herpes simplex virus 1 & 2 glycoprotein D gene amplified by the primer set 1 comprising of SEQ ID No 1 and 2 FP: 5' cgcttggtttcggatgggag 3' (SEQ ID No.1) & RP: 5' gcccccagagacttgttgtagg 3' (SEQ ID No.2)
2. Herpes simplex virus 1 & 2 UL 44 gene amplified by the primer set 2 comprising of SEQ ID No 3 and 4 FP: 5' ggcaatcgtgtacgtcgtccg 3' (SEQ ID No.3) & RP: 5' cggggggggtcttgcgttac 3' (SEQ ID No.4)
3. Herpes simplex virus 1 & 2 DNA polymerase gene amplified by the primer set 3 comprising of SEQ ID No 5 and 6 FP: 5' caagctgacggacatttacaagg 3' (SEQ ID No.5) & RP: 5' gtcccacacgcgaaacacg 3' (SEQ ID No.6)
4. Cytomegalovirus Glycoprotein O gene amplified by the primer set 4 comprising of SEQ ID No 7 and 8 FP: 5' ttccggctcatggcgttaacc 3' (SEQ ID No.7) & RP: 5' cgccctgctttacgttacgc 3' (SEQ ID No.8)
5. Cytomegalovirus Morphological transformation gene amplified by the primer set 5 comprising of SEQ ID No 9 and 10 FP: 5' cggcgacgacgacgataaag 3' (SEQ ID No.9) & RP: 5' caatctggtcgcgtaatcctctg 3' (SEQ ID No.10)
6. Cytomegalovirus UL 88 gene amplified by the primer set 6 comprising of SEQ ID No 11 and 12 FP: 5' gggcacgtcctcgcagaag 3' (SEQ ID No.11) & RP: 5' ccaagatgcaggtgataggtgac 3' (SEQ ID No.12)
7. Varicella zoster ORF 29 amplified by the primer set 7 comprising of SEQ ID No 13 and 14 FP: 5' ggtcttgccggagctggtattac 3' (SEQ ID No.13) & RP: 5' tgcctccgtgaaagacaaagaca 3' (SEQ ID No.14)
8. Varicella zoster DNA polymerase gene amplified by the primer set 8 comprising of SEQ ID No 15 and 16 FP: 5' tccatttaacgttgcatcattttgtg 3' (SEQ ID No.15) & RP: 5' acgttccggtagcgagttatctg 3' (SEQ ID No.16)
9. Adenoviruses Hexon Gene amplified by the primer set 9 comprising of SEQ ID No 17 and 18 FP: 5' cgccgccaacatgctctacc 3' (SEQ ID No.17) & RP: 5' gttgcgggagggatggata 3' (SEQ ID No.18)
10. Eubacterial 16s ribosomal RNA gene region I amplified by the primer set 10 comprising of SEQ ID No 19 and 20 FP: 5' tgggctacacacgtgctacaatgg 3' (SEQ ID No.19) & RP: 5' cggactacgatcggttttgtgaga 3' (SEQ ID No.20).
11. Eubacterial 16s ribosomal RNA gene region II amplified by the primer set 11 comprising of SEQ ID No 21 and 22 FP: 5' ggcctaacacatgcaagtcgagc 3 (SEQ ID No.21) & RP: 5' ggcagattcctaggcattactcacc 3 (SEQ ID No.22)
12. Gram+ve bacterial specific portion of 16s ribosomal RNA gene amplified by the primer set 12 comprising of SEQ ID No 23 and 24 FP: 5' acgtcaaatcatcatgcccccttat 3' (SEQ ID No.23) & RP: 5' tgcagcccttttgtaccgtccat 3' (SEQ ID No.24)
13. *Mycobacterium tuberculosis* MPB 64 gene amplified by the primer set 13 comprising of SEQ ID No 25 and 26 FP: 5' gcggaacgtgggaccaatac 3' (SEQ ID No.25) & RP: 5' cgacggggtgattttcttcttc 3' (SEQ ID No.26)
14. *Mycobacterium fortuitum* 16s-23s RNA gene amplified by the primer set 14 comprising of SEQ ID No 27 and 28 FP: 5' aactttttttgactgccagacacactattg 3' (SEQ ID No.27) & RP: 5' ggatgccacccccccaaaag 3' (SEQ ID No.28)
15. *Mycobacterium chelonae* 16s-23 s RNA gene amplified by the primer set 15 comprising of SEQ ID No 29 and 30 FP: 5' tggttactcgcttggtgaatatgt 3' (SEQ ID No.29) & RP: 5' gacgttttgccgactacctatcc 3 (SEQ ID No.30)
16. *Toxoplasma gondii* B 1 gene amplified by the primer set 17 comprising of SEQ ID No 31 and 32 FP: 5' cccctctgctggcgaaaagtg 3' (SEQ ID No.31) & RP: 5' ggcgaccaatctgcgaatacac 3' (SEQ ID No.32)
17. *Chlamydia trachomatis* polymorphic protein II amplified by the primer set 18 comprising of SEQ ID No 33 and 34 FP:5' aatcgtatctcgggttaatgttgc 3' (SEQ ID No.33) & RP:5' tcgaggaaaaccgtatgagaaac 3' (SEQ ID No.34)
18. Fungal specific portion of 28s ribosomal RNA gene amplified by the primer set 19 comprising of SEQ ID No 35 and 36 FP: 5' gctgggactgaggactgcgac 3' (SEQ ID No.35) & RP: 5' ttcaagacgggcggcatataac 3(SEQ ID No.36)
19. *Propionibacterium acnes* specific portion of 16s-23s ribosomal RNA gene amplified by the primer set 20 comprising of SEQ ID No 37 and 38 FP: 5' tggcgaacgggtgagtaaca 3' (SEQ ID No.37) & RP: 5' ccggtattagccccagtttcc 3' (SEQ ID No.38)

20. Gram−ve bacterial specific portion of gyr B gene amplified by the primer set 21 comprising of SEQ ID No 39 and 40 FP: 5' cggcggcaagttcgacgac 3' (SEQ ID No.39) & RP: 5' ccaccgagacgcccacacc 3' (SEQ ID No.40)

21. Gram−ve bacterial aconitate hydratase gene amplified by the primer set 22 comprising of SEQ ID No 41 and 42 FP: 5' ccaggtcggcggagaagc 3' (SEQ ID No.41) & RP: 5' ccaccggcccgatgacc 3' (SEQ ID No.42)

22. Gram−ve ribonuclease 1 gene amplified by the primer set 23 comprising of SEQ ID No 43 and 44 FP: 5' gccgccctgaccaccttc 3' (SEQ ID No.43) & RP: 5' gcgggttgttcggcatcag 3' (SEQ ID No.44)

In another embodiment of this invention the probe sequences with SEQID 45-67 were obtained by computer programs used to design the primers for identification of specific gene segments that are unique to pathogens mentioned. The probe sequences vary in length from 66-90 nucleotides. The probes do not form hairpin loops within themselves. They share no homology with any other amplicons. The probes can be amplified from either of the strands of pathogen DNA.

The probe sequences are detailed as below:

1. Probe DNA sequence "cgcttggtttcggatgggaggcaactgtgctatcccatcacggtcatggagta-caccgaatgacctacaacaagtctctggg ggc" (SEQ ID No. 45) of Herpes simplex virus 1 & 2 glycoprotein D gene (amplified by the primer set 1 comprising of FP: 5' cgcttggtttcggatgggag 3' (SEQ ID No.1) & RP: 5' gcccccagagacttgttgtagg 3' (SEQ ID No.2))

2. Probe DNA sequence "ggcaatcgtgtacgtcgtccgcacatca-cagtcgcggcagcgtcatcggcggtaacgcaagaccccccg" (SEQ ID No. 46) of Herpes simplex virus 1 & 2 UL 44 gene (amplified by the primer set 2 comprising of FP: 5' ggcaatcgtgtacgtcgtccg 3' (SEQ ID No.3) & RP: 5' cgggggggtcttgcgttac 3' (SEQ ID No.4)

3. Probe DNA sequence "caagctgacggacatllacaaggtc-cccctggacgggtacggccgcatgaacg-gccggggcgtgtttcgcgtgtgggac" (SEQ ID No. 47) of Herpes simplex virus 1 & 2 DNA polymerase gene (amplified by the primer set 3 comprising of FP: 5' caagctgacggacatttacaagg 3' (SEQ ID No.5) & RP: 5' gtcccacacgcgaaacacg 3' (SEQ ID No.6))

4. Probe DNA sequence "ttccggctcatggcgttaaccaggta-gaaactgtgtgtacagttgcgttgtgcgtaacgtaaaagcagggcg" (SEQ ID No. 48) of Cytomegalovirus Glycoprotein O gene (amplified by the primer set 4 comprising of FP: 5' ttccggctcatggcgttaacc 3' (SEQ ID No.7) & RP: 5' cgc-cctgcttttacgttacgc 3' (SEQ ID No.8))

5. Probe DNA sequence "cggcgacgacgacgataaagaata-caaagccgcagtgtcgtccagagggattacgcgaccagattg" (SEQ ID No.49) of Cytomegalovirus Morphological transforming region II gene amplified by the primer set 5 comprising of FP: 5' cggcgacgacgacgataaag 3' (SEQ ID No.9) & RP: 5' caatctggtcgcgtaatcctctg 3' (SEQ ID No.10)

6. Probe DNA sequence "gggcacgtcctcgcagaaggactccagg-tacaccttgacgtactggtcacctatcacctgcatatgg" (SEQ ID No.50) of Cytomegalovirus UL 88 gene (amplified by the primer set 6 comprising of FP: 5' gggcacgtcctcgca-gaag 3' (SEQ ID No.11) & RP: 5' ccaagatgcaggtgatag-gtgac 3' (SEQ ID No.12))

7. Probe DNA sequence "ggtatgccggagctggtattacct-taaaactcactaccagtcatttctatccatctgtctttgtctttcacggaggca" (SEQ ID No. 51) of Varicella zoster ORF 29 (amplified by the primer set 7 comprising of FP: 5' ggtcttgccg-gagctggtattac 3' (SEQ ID No.13) & RP: 5' tgcctccgt-gaaagacaaagaca 3' (SEQ ID No.14))

8. Probe DNA sequence "tccatttaacgttgcatcattttgtgt-tatcatagaactgcgtaaacactcg-gcaagtaatacagataactcgctaccggaacgt" (SEQ ID No. 52) Varicella zoster DNA polymerase gene (amplified by the primer set 8 comprising of FP: 5' tccatttaacgttgcat-cattttgtg 3' (SEQ ID No.15) & RP: 5' acgttccggtagcgagt-tatctg 3' (SEQ ID No.16))

9. Probe DNA sequence "cgccgccaacatgctctaccctatac-ccgccaacgctaccaacgtgcccatatccatccctcccgcaac" (SEQ ID No. 53) of Adenoviruses Hexon Gene (amplified by the primer set 9 comprising of FP: 5' cgccgccaacatgctc-tacc 3' (SEQ ID No.17) & RP: 5' gttgcgggaggggatggata 3' (SEQ ID No.18))

10. Probe DNA sequence "tgggctacacacgtgctacaatggtcgg-tacagagggtcgccaaaccgcgaggtg-gagctaatctcacaaaaccgatcgta gtccg" (SEQ ID No. 54) of Eubacterial 16s ribosomal RNA gene region I (amplified by the primer set 10 comprising of FP: 5' tgggctaca-cacgtgctacaatgg 3' (SEQ ID No.19) & RP: 5' cggactac-gatcggttttgtgaga 3' (SEQ ID No.20)).

11. Probe DNA sequence "ggcctaacacatgcaagtcgagcggat-gaaaggagcttgacctggattcagcg-gcggacgggtgagtaatgcctaggaatctgcc" (SEQ ID No. 55) of Eubacterial 16s ribosomal RNA gene region II (amplified by the primer set 11 comprising of FP: 5' ggcctaa-cacatgcaagtcgagc 3 (SEQ ID No.21) & RP: 5' ggcagat-tcctaggcattactcacc 3 (SEQ ID No.22))

12. Probe DNA sequence "acgtcaaatcatcatgcccccttatgac-ctgggctacacacgtgctacaatggacggtacaaagggctgca" (SEQ ID No. 56) of Gram+ve bacterial specific portion of 16s ribosomal RNA gene (amplified by the primer set 12 comprising of FP: 5' acgtcaaatcatcatgccccctttat 3' (SEQ ID No.23) & RP: 5' tgcagcccttttgtaccgtccat 3' (SEQ ID No.24))

13. Probe DNA sequence "gcggaacgtgggaccaatacctgggt-tgggccggctgcttcgggcagcaactc-ccccgggttgaagaagaaaatcaccccgtcg" (SEQ ID No. 57) of *Mycobacterium tuberculosis* MPB 64 gene (amplified by the primer set 13 comprising of FP: 5' gcggaacgtgg-gaccaatac 3' (SEQ No.25) & RP: 5' cgacggggtgattttct-tcttc 3' (SEQ ID No.26))

14. Probe DNA sequence "aactttttgactgccagacacactat-tgggctttgagacaacaggcccgtgcccctttgggggtggcatcc" (SEQ ID No. 58) of *Mycobacterium fortuitum* 16s-23s RNA gene (amplified by the primer set 14 comprising of FP: 5' aactttttgactgccagacacactattg 3' (SEQ ID No.27) & RP: 5' ggatgccaccccccaaaag 3' (SEQ ID No.28))

15. Probe DNA sequence "tggttactcgcttggtgaatatgttt-tataaatcctgtccaccccgtggataggtagtcggcaaaacgtc" (SEQ ID No. 59) of *Mycobacterium chelonae* 16s-23 s RNA gene (amplified by the primer set 15 comprising of FP: 5' tggttactcgcttggtgaatatgt 3' (SEQ ID No.29) & RP: 5' gacgttttgccgactacctatcc 3 (SEQ ID No.30))

16. Probe DNA sequence "cccctctgctggcgaaaagtgaaat-tcatgagtatctgtgcaactttggtgtattcgcagattggtcgcc" (SEQ ID No. 60) of *Toxoplasma gondii* B 1 gene (amplified by the primer set 16 comprising of FP: 5' cccctctgctggc-gaaaagtg 3' (SEQ ID No.31) & RP: 5' ggcgaccaatctgc-gaatacac 3' (SEQ ID No.32))

17. Probe DNA sequence "aatcgtatctcgggttaatgttgcat-gatgctttatcaaatgacaagcttagatccgtttctcatacggttttcctcga" (SEQ ID No. 61) of *Chlamydia trachomatis* polymorphic protein II (amplified by the primer set 17 comprising of FP:5' aatcgtatctcgggttaatgttgc 3' (SEQ ID No.33) & RP:5' tcgaggaaaaccgtatgagaaac 3' (SEQ ID No.34))

18. Probe DNA sequence "gctgggactgaggactgcgacgtaagt-caaggatgctggcataatggttatatgccgcccgtcttgaa" (SEQ No. 62) of Fungal specific portion of 28s ribosomal RNA. gene (amplified by the primer set 18 comprising of FP: 5' gctgggactgaggactgcgac 3' (SEQ ID No.35) & RP: 5' ttcaagacgggcggcatataac 3 (SEQ ID No.36))

19. Probe DNA sequence "tggcgaacgggtgagtaacacgtgag-taacctgcccttgactttgggataacttcaggaaactggggctaataccgg" (SEQ ID No. 63) of Propionibacterium acnes specific portion of 16s-23s ribosomal RNA gene (amplified by the primer set 19 comprising of FP: 5' tggcgaacgggtgag-taaca 3' (SEQ ID No.37) & RP: 5' ccggtattagccccagtttcc 3' (SEQ ID No.38))

20. Probe DNA sequence "cggcggcaagttcgacgacaacaccta-caaggtgtccggcggcttgcacggtgtgggcgtctcggtgg" (SEQ ID No. 64) of Gram−ve bacterial specific portion of gyr B gene (amplified by the primer set 20 comprising of FP: 5' cggcggcaagttcgacgac 3' (SEQ ID No.39) & RP: 5' ccac-cgagacgcccacacc 3' (SEQ ID No.40))

21. Probe DNA sequence "ccaggtcggcggagaagccgaggcag-gcgaggtccttcagttcgtcgcgggtcatcgggccggtgg" (SEQ ID No. 65) of Gram−ve bacterial aconitate hydratase gene (amplified by the primer set 21 comprising of FP: 5' ccaggtcggcggagaagc 3' (SEQ ID No.41) & RP: 5' ccac-cggcccgatgacc 3' (SEQ ID No.42))

22. Probe DNA sequence "gccgccctgaccaccttcatcagcctg-gccggccgttacctggtgctgatgccgaacaacccgc" (SEQ ID No. 66) of Gram−ve ribonuclease 1 (gene amplified by the primer set 22 comprising of FP: 5' gccgccctgaccaccttc 3' (SEQ ID No.43) & RP: 5' gcgggttgttcggcatcag 3' (SEQ ID No.44))

It seems to be repetition

In another embodiment of this invention target sequences with SEQ ID Nos 67-88 were generated from the probe sequences using computer programs. These targets are used for immobilization on inert matrices such as nylon and cross-linked using UV-radiation or chemical fixation. The targets were chosen according to the following criteria:

1. All the target sequences are pathogen specific and do not overlap with any other sequences of other pathogens.
2. All the target sequences are in the size range of 23 to 38 bases long
3. All the targets have uniform melting temperatures in the range of 58.9° C.-88° C.
4. The target sequences reside in the amplicon region and do not contain forward or reverse primer sequences so that labeled probes (with SEQ ID Nos 67-91) do not bind non-specifically to these targets.
5. All the targets are designed in such a way that they match all the nucleotide bases generally. However if there is mismatch in some of the probes the mismatch is limited to maximum of two nucleotides in the middle of the probe so as to ensure hybridization.

The target sequences are described in detail below:

1. 5'gcaactgtgctatccccatcacggtcatggagtacaccgaatgct3' (SEQ ID No. 67) the target for HSV glycoprotein D amplified by the primer set 1
2. 5'cacatcacagtcgcggcagcgtcatcggcg 3' (SEQ ID No. 68) the target for HSV UL 44 amplified by the primer set 2
3. 5'tccccctggacgggtacggccgcatgaacggccgggg 3' (SEQ ID No. 69) the target for HSV polymerase gene amplified by the primer set 3
4. 5'aggtagaaactgtgtgtacagttgcgttgtg 3' (SEQ ID No. 70) the target for glycoprotein O of CMV amplified by primer set 4
5. 5'aatacaaagccgcagtgtcgtc 3' (SEQ ID No. 71) the target for morphological transforming gene II of Cytomegalovirus amplified by the primer set 5
6. 5'gactccaggtacaccttgacgtactg 3' (SEQ ID No. 72) the target for UL 88 gene of Cytomegalovirus amplified by primer set 6
7. 5'cttaaaactcactaccagtcatttctatccatc 3' (SEQ ID No. 73) the target for ORF 29 gene of Varicella zoster virus amplified by the primer set 7
8. 5'ttatcatagaactgcgtaaacactcggcaagtaata 3' (SEQ II) No. 74) the target for DNA polymerase gene of Varicella zoster virus amplified by the primer set 8
9. 5' ctataccgccaacgctaccaacgtgccca 3' (SEQ ID No. 75) the target for Hexon gene of Adenoviruses amplified by primer set 9
10. 5'tcggtacagagggtcgccaaaccgcgaggtggagctaa 3' (SEQ ID No. 76) the target for Eubacterial 16 s ribosomal gene region I amplified by the primer set 10
11. 5'ggatgaaaggagcttgctcctggattcagcggcggacg 3' (SEQ ID No. 77) the target for Eubacterial 16 s ribosomal gene region II amplified by the primer set 11
12. 5' gacctgggctacacacgtgctaca 3' (SEQ ID No. 78) the target for the 16s ribosomal gene of gram-positive organisms amplified by the primer set 12
13. 5'ctgggttgggccggctgatcgggcagcaactcccccgggtt 3' (SEQ ID No. 79) the target for the MPB 64 gene of *Mycobacterium tuberculosis* amplified by the primer set 13
14. 5' ggctttgagacaacaggcccgtgccc 3' (SEQ ID No. 80) the target for 16s-23s RNA gene of *Mycobacterium fortuitum* amplified by the primer set 14
15. 5' tttataaatcctgtccaccccgt 3' (SEQ ID No. 81) the target for the 16s-23s RNA gene of *Mycobacterium chelonae* amplified by the primer set 15
16. 5' aaattcatgagtatctgtgcaactttg 3' (SEQ ID No. 82) the target for B1 gene of *Toxoplasma gondii* amplified by the primer set 16
17. 5' atgatgctttatcaaatgacaagcttagatcc 3' (SEQ ID No. 83) the target for polymorphic protein II of *Chlamydia trachomatis* amplified by the primer set 17
18. 5' gtaagtcaaggatgctggcataatg 3' (SEQ ID No. 84) the target for the 28s ribosomal RNA gene of all fungi amplified by the primer set 18
19. 5' gcttcagcgccgtcagcgaggataac 3' (SEQ ID No. 85) the target for the 16s ribosomal RNA gene of *Propionibacterium acnes* amplified by the primer set 19
20. 5' aacacctacaaggtgtccggccggcttgcac 3' (SEQ ID No. 86) the target for gyrase gene of gram−ve organisms amplified by the primer set 20
21. 5' cgaggcaggcgaggtccttcagttcgtcgcg 3' (SEQ ID No. 87) the target for aconitate hydratase gene of gram−ve organisms amplified by the primer set 21
22. 5' atcagcctggccggccgttacctggtg 3' (SEQ ID No. 88) the target for the ribonuclease gene of gram−ve organisms amplified by the primer set 22

These oligonucleotides reported above and used for immobilization on inert matrix were confirmed (by sequence analyses) using products generated from standard DNA as well as clinical samples. These sequences are unique and not are not known or described for either multiplex or uniplex PCR.

In yet another embodiment of the present invention a multiplex PCR assay is provided using all or a few primer sets as aforesaid where in all the primers can be used together in a single tube using uniform thermal cycling conditions, comprising of a denaturing step of 94° C. for 5 minutes, followed by 40 cycles of 45 seconds at 60° C.-64° C., 45 seconds at 72° C. and 45 seconds at 94° C. followed by 10 minutes extension of the reaction at 72° C.

In a further embodiment, the set of primers, which are labeled at 5' end using a biotin moiety enabling detection of coloured product.

In still another embodiment, the said primers are labeled by fluorescent labels such as organic fluorescent labels e.g., Fluorescene isothiocyanate FITC or inorganic fluorescent nano-particles such as Quantum Dots™ or Cy3 or Cy5 enabling detection by any fluorescent scanning device or microscopy.

In another, embodiment the present invention provides the use of the said pool of primers and probes wherein the assay is a real time PCR for detection of the pathogens.

In yet another embodiment the present invention provides the use of the said pool of primers and probes wherein the assay is a real time PCR for quantification of pathogen in a clinical sample for monitoring prognosis or therapy of the disease.

In still another embodiment the present invention provides the use of the said pool of primers wherein the detection of the amplified product could be in the form of a macroarray or a slot blot or line probe assay.

In a further embodiment the present invention provides a macroarray consisting of the said probes fixed to a solid phase comprising of nitrocellulose, nylon, charged nylon, glass, or polystyrene.

In another embodiment the present invention provides a method for the detection and discrimination of pathogens causing syndromes such as infectious endophthalmitis or keratitis or uveitis or retinitis or meningitis, wherein the pathogens to be detected are Herpes simplex viruses 1 and 2, cytomegaloviruses, Varicella Zoster virus, Adenoviruses, Eubacteria, Gram-positive organisms, Gram-negative bacteria, Fungi, *Mycobacterium tuberculosis, Mycobacterium chelonei, Mycobacterium fortuitum, Toxoplasma gondii, Chlamydia trachomatis.*

In still another embodiment the present invention provides a method for the detection of an individual pathogen amongst a group of probable pathogens causing an eye or nervous system diseases with similar manifestations.

In yet another embodiment the present invention provides any multiplex PCR assay using a select few or all of the primers as aforesaid, wherein any clinical syndrome caused by a few or all of the said organisms is being investigated for the detection of any one individual pathogen or groups of pathogens present in the clinical specimen.

In a further embodiment the present invention provides a method for the simultaneous detection of all the pathogens causing external ocular infection, endophthalmitis or uveitis or retinitis or meningoencephalitis comprising:

[a] obtaining a clinical sample from patient suffering from the said infections;
[b] extracting DNA from a portion of or total sample as obtained in step [a];
[c] conducting a multiplex PCR for the DNA as obtained in claim [b] using a pool of primers as claimed in claim 1, labeled with biotin or fluorescent tracers and standard reagents of PCR;
[d] denaturation of the PCR product as obtained from step [c];
[e] hybridizing the PCR products as obtained in step [d] with targets immobilized on a solid matrix;
[f] detecting the DNA hybrids on the solid matrix as obtained in step [e] by enzymatic or fluorescent methods In another embodiment the present invention provides a kit for the simultaneous detection of all the pathogens causing external ocular infection, endophthalmitis or uveitis or retinitis or meningo-encephalitis comprising:

a) a pool of forward and reverse primers as aforesaid;
b) a matrix of DNA targets as aforesaid immobilized on a suitable solid support;
c) standard reagents required for the amplification of DNA by polymerase chain reaction;
d) standard reagents required for hybridizing the PCR amplified products to the immobilized matrix of DNA probes;
e) standard reagents required to detect the final hybridized products for the detection and discrimination of the specific causative pathogen(s).

In a further embodiment the present invention provides a method for the simultaneous detection of all the pathogens causing external ocular infection, endophthalmitis or uveitis or retinitis or meningoencephalitis comprising:

[a] obtaining a clinical sample from patient suffering from the said infections;
[b] extracting DNA from a portion of or total sample as obtained in step [a];
[c] conducting a multiplex PCR for the DNA as obtained in claim [b] using a pool of primers as aforesaid, labeled with biotin or fluorescent tracers and standard reagents of PCR;
[d] denaturation of the PCR product as obtained from step [c];
[e] hybridizing the PCR products as obtained in step [d] with the targets as aforesaid immobilized on a solid matrix;
[f] detecting the DNA hybrids on the solid matrix as obtained in step [e] by enzymatic or fluorescent methods.

EXAMPLES

The following examples are given by way of illustration of the present invention and therefore should not be construed to limit the scope of the present invention.

Example 1

A multiplex PCR was carried out with primer sets 9 and 18, which can amplify the hexon gene of adenoviruses and polymorphic protein II gene of *Chlamydia trachomatis* respectively. The PCR mix contained 10 to 20 pmoles each of the forward and reverse primers, 200 μM of each d-ATP, d-UTP, d-CTP and d-GTP, 2 units of Taq polymerase in 10 mM Tris-HCl pH 9.0, 1.5 mM MgCl$_2$, 5 mM KCl, 0.01% gelatin, 1 mM EDTA and 1 unit of UDP glycosylase to prevent amplicon contamination. The cycling conditions are being incubation at 37° C. for 30 minutes for complete digestion of any amplicon contaminants, 2 minutes at 50° C., a denaturing step of 94° C. for 5 minutes, followed by 40 cycles of 45 seconds at 60° C., 45 seconds at 72° C. and 45 seconds at 94° C. followed by 10 minutes extension of the reaction at 72° C. The product was analysed by 6% agarose gel. As can be seen in FIG. 1 both the genes got amplified. Standard DNA of 1 pg of adenovirus and 10 fg of *Chlamydial* DNA was used for amplification.

FIG. 1 shows 6% Agarose gel electrophoretogram showing the amplified products of uniplex & multiplex PCR for Hexon gene of Adenovirus & *C. trachomatis* genome.

Example 2

Figure 2:
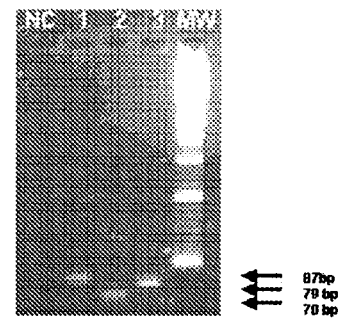
FIG. 2 shows 4% Agarose gel electrophoretogram showing the amplified products of glycoprotein D, DNA polymerase, UL-44 regions of Herpes Simplex Virus (HSV).

A multiplex PCR was carried out with primer sets 1, 2 and 3, which can amplify the Glycoprotein D, UL 44 and DNA Polymerase genes respectively. The PCR mix contained 10 pmoles each of the forward and reverse primers, 200 µM of each d-ATP, d-UTP, d-CTP and d-GTP, 2 units of Taq polymerase in 10 mM Tris-HCl pH 7.5, 1.5 mM MgCl$_2$, 5 mM KCl, 0.01% gelatin, 1 mM EDTA and 1 unit of UDP glycosylase to prevent amplicon contamination. The cycling conditions are being incubation at 37° C. for 30 minutes for complete digestion of any amplicon contaminants, 2 minutes at 50° C. a denaturing step of 94° C. for 5 minutes, followed by 40 cycles of 45 seconds at 60° C., 45 seconds at 72° C. and 45 seconds at 94° C. followed by 10 minutes extension of the reaction at 72° C. The product was analysed by 6% agarose gel. As can be seen in FIG. 2 all the three genes got amplified FIG. 2 shows 4% Agarose gel electrophoretogram showing the amplified products of glycoprotein D, DNA polymerase, UL-44 regions of Herpes Simplex Virus (HSV).

Example 3

Figure 3:
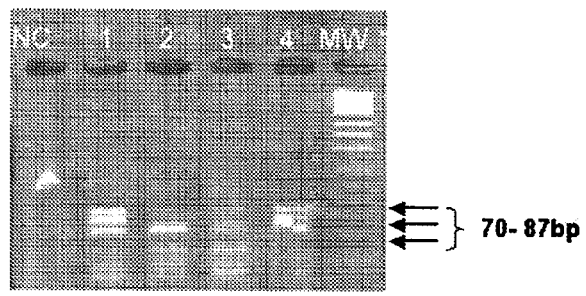
FIG. 3 shows 6% Agarose gel electrophoretogram showing the amplified products of multiplex PCR for External ocular infections.

A multiplex PCR was carried out with primer sets 1, 2, 3, 9 and 17 which can amplify the Glycoprotein D gene, UL 44 gene and DNA Polymerase genes of HSV, hexon gene of adenoviruses and polymorphic protein II gene of *Chlamydia trachomatis* respectively. The PCR mix contained 10 pmoles each of the forward and reverse primers, 200 µM of each d-ATP, d-UTP, d-CTP and d-GTP, 2 units of Taq polymerase in 10 mM Tris-HCl pH 9.0, 1.5 mM MgCl$_2$, 5 mM KCl, 0.01% gelatin, 1 mM EDTA and 1 unit of UDP glycosylase to prevent amplicon contamination. The cycling conditions are being incubation at 37° C. for 30 minutes for complete digestion of any amplicon contaminants, 2 mins at 50° C. and a denaturing step of 94° C. for 5 minutes, followed by 40 cycles of 45 seconds at 60° C., 45 seconds at 72° C. and 45 seconds at 94° C. followed by 10 minutes extension of the reaction at 72° C. Five tubes of the PCR mix mentioned above were incubated with the following DNA preparations where in the tube NC did not received any DNA tube 1 received 1 picogram of HSV DNA, tube 2 received 4 femtograms of *C. trachomatis* tube 3 received 10 picograms of adenoviral DNA and tube 4 received all three DNAs in the quantities mentioned. The product were analysed by 6% agarose gel. As can be seen in FIG. 3 all genes got amplified.

FIG. 3 shows 6% Agarose gel electrophoretogram showing the amplified products of multiplex PCR for External ocular infections.

Figure 4:
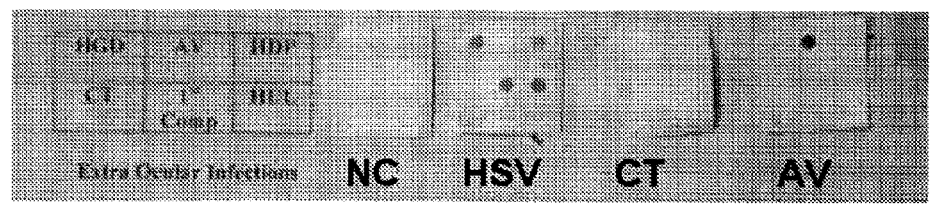
FIG. 4 shows the macro-array spotted on nylon membranes hybridized with amplicons from multiplex PCR for identification of external ocular infections specifically identifying genomes of HSV, *C. trachomatis*, Adenovirus.

MW—Hinf I digest of φx 174 DNA Nylon membranes each spotted with 100 p moles of targets with SEQ ID No. 67, 68, 69, 75 and 83 in 0.26 N NaOH (FIG. 4). The membrane was then blocked using 2×SSPE containing 0.1% SDS and 1% BSA for one hour at 37° C. The amplicons were heated to 95° C. for 10 mins and mixed in 2×SSPE containing 0.1% SDS and hybridized for 2 hours at 52° C. After hybridization the membrane was washed five times for three minutes each in 1×SSPE containing 0.1% SDS. The membrane was incubated with Streptavidin peroxidase conjugate in 0.1 M Tris-HCl pH 7.4 containing 1% BSA, 150 mM NaCl and 0.3% tween-20. After 30 minutes at 37° C. the membrane was washed five times three minutes each with the same buffer. For development of color, the membrane was incubated for 10 minutes at 37° C. with 0.5 mg of Diaminobenzidine HCl per ml of phosphate buffered saline. The appearance of brown colored spots indicate the presence of specific pathogen.

FIG. 4 shows the macro-array spotted on nylon membranes hybridized with amplicons from multiplex PCR for identification of external ocular infections specifically identifying genomes of HSV, *C. trachomatis*, Adenovirus.

DNA Arrays (Left to Right): Template of the DNA probe spotting on nylon membranes. HSV—Herpes Simplex virus showing spots labeled as HGD=HSV glycoprotein D; HDP=HSV DNA Polymerase; HUL=UL 44 gene; 1$^{st}$ Comp.=Complementary strand probe of HGD, CT—*C. trachomatis*. AV—Adenovirus. NC—Negative control, HSV-membrane hybridized with amplicon from tube 1. CT-Membrane hybridized with amplicon from tube 2; AV-membrane hybridized with amplicon from tube 3

Example 4

Figure 5:
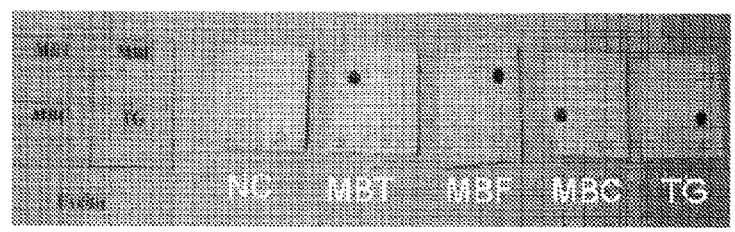
FIG. 5 shows the macro-array spotted on nylon membranes hybridized with amplicons of multiplex PCR for detection of uveitis & other suspected mycobacterial infections specifically identifying genomes of *T. gondii, M. tuberculosis M. fortuitum* and *M. Chelonae*.

A multiplex PCR was carried out with primer sets 13, 14, 15 and 16 which can amplify the MPB 64 gene of *Mycobacterium tuberculosis*, 16s-23s RNA gene of Mycobacterium fortuitum, 16s-23s RNA gene of *Mycobacterium chelonae* and B1 gene of *Toxoplasma gondii*. The PCR mix contained 10 pmoles each of the forward and reverse primers, 200 µM of each d-ATP, d-UTP, d-CTP and d-GTP, 2 units of Taq polymerase in 50 mM Tris-HCl pH 9.0, 1.5 mM MgCl$_2$, 5 mM KCl, 0.01% gelatin, 1 mM EDTA and 1 unit of UDP glycosylase to prevent amplicon contamination. The cycling conditions are being incubation at 37° C. for 30 minutes for complete digestion of any amplicon contaminants, 2 minutes at 50° C. and a denaturing step of 94° C. for 5 minutes, followed by 40 cycles of 45 seconds at 60° C., 45 seconds at 72° C. and 45 seconds at 94° C. followed by 10 minutes extension of the reaction at 72° C. Five tubes of the PCR mix mentioned above were incubated with the following DNA preparations where in the tube NC did not received any DNA, tube 1 received 1 femtograms of *M. tuberculosis* DNA, tube 2 received 100 femtograms of *M. fortuitum* DNA tube 3 received 100 femtograms of *M. chelonae* DNA, tube 4 received 1 fgs of *Toxoplasma gondii* DNA. FIG. 5 shows five nylon membranes each spotted with 100 p moles of targets with SEQ ID No 79, 80, 81 and 82 in 0.26 N NaOH. The membrane was then blocked using 2×SSPE containing 0.1% SDS and 1% BSA for one hour at 37° C. The amplicons were heated to 95° C. for 10 mins and mixed in one ml of 2×SSPE containing 0.1% SDS and hybridized for 2 hours at 52° C. After hybridization the membrane was washed five times for three minutes each in 1×SSPE containing 0.1% SDS. The membrane was incubated with Streptavidin peroxidase conjugate in 0.1 M Tris-HCl pH 7.4 containing 1% BSA, 150 mM NaCl and 0.3% tween-20. After 30 minutes at 37° C. the membrane was washed five times three minutes each with the same buffer. For development of color, the membrane was incubated for 10 minutes at 37° C. with 0.5 mg of Diaminobenzidine HCl per ml of phosphate buffered saline. The appearance of brown colored spots indicate the presence of specific pathogen.

FIG. 5 shows the macro-array spotted on nylon membranes hybridized with amplicons of multiplex PCR for detection of uveitis & other suspected mycobacterial infections specifically identifying genomes of *T. gondii, M. tuberculosis M. fortuitum* and *M. Chelonae*.

From left to right first is the template showing how the targets had been spotted on membrane. MBT—*M. tuberculosis* MBF—*M. fortuitum* MBC—*M. chelonae* TG—*T. gondii*. Second is NC hybridized with negative control tube labeled as NC. Nylon membranes hybridized with amplicons obtained from Tube 1, 2, 3 and 4 are labeled as MBT, MBF, MBC and TG respectively Example 5

A multiplex PCR was carried out with primer sets 1, 2, 3, 4, 5, 6, 7 and 8 which can amplify the Glycoprotein D gene, UL 44 gene and DNA Polymerase genes of HSV, Glycoprotein O gene, Morphological transformation and UL 88 genes of CMV and ORF29 gene and DNA polymerase gene of VZV respectively. The PCR mix contained 10 pmoles each of the forward and reverse primers, 200 µM of each d-ATP, d-UTP, d-CTP and d-GTP, 2 units of Taq polymerase in 10 mM Tris-HCl pH 9.0, 1.5 mM $MgCl_2$, 5 mM KCl, 0.01% gelatin, 1 mM EDTA and 1 unit of UDP glycosylase to prevent amplicon contamination. The cycling conditions are being incubation at 37° C. for 30 minutes for complete digestion of any amplicon contaminants, 2 minutes at 50° C. and a denaturing step of 94° C. for 5 minutes, followed by 40 cycles of 45 seconds at 60° C., 45 seconds at 72° C. and 45 seconds at 94° C. followed by 10 minutes extension of the reaction at 72° C.

Figure 6:
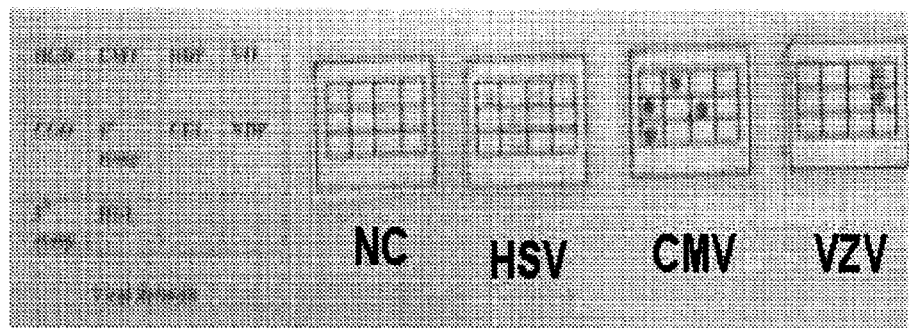
FIG. 6 shows the macro-array spotted on nylon membranes hybridized with amplicons from multiplex PCR for identification of rival retinitis specifically identifying genomes of HSV, CMV, and VZV.

Four tubes of the PCR mix mentioned above were incubated with the following DNA preparations where in the tube NC did not received any DNA, tube 1 received 1 picogram of HSV DNA, tube 2 received 10 picogram of CMV DNA and tube 3 received 1 pg of VZV DNA. FIG. 6 shows four nylon membranes each spotted with 100 p moles of targets with SEQ ID No. 67, 68, 69, 70, 71, 72, 73 and 74 in 0.26 N NaOH. The membrane was then blocked using 2×SSPE containing 0.1% SDS and 1% BSA for one hour at 37° C. The amplicon was heated to 95° C. for 10 mins and mixed in 2×SSPE containing 0.1% SDS and hybridized for 2 hours at 52° C. After hybridization the membrane was washed five times for three minutes each in 1×SSPE containing 0.1% SDS. The membrane was incubated with Streptavidin peroxidase conjugate in 0.1 M Tris-HCl pH 7.4 containing 1% BSA, 150 mM NaCl and 0.3% tween-20. After 30 minutes at 37° C. the membrane was washed five times three minutes each with the same buffer. For development of color, the membrane was incubated for 10 minutes at 37° C. with 0.5 mg of Diaminobenzidine HCl per ml of phosphate buffered saline. The appearance of brown colored spots indicates the presence of specific pathogen.

FIG. 6 shows the macro-array spotted on nylon membranes hybridized with amplicons from multiplex PCR for identification of rival retinitis specifically identifying genomes of RSV, CMV, and VZV.

Left to right Template of how the probes are spotted on each nylon membrane. HSV—Herpes Simplex virus showing HGD=HSV glycoprotein D, HDP=HS DNA Polymerase HUL=UL 44 gene $1^{st}$ Comp.=Complementary strand probe of HGD CMV—Cytomegalovirus showing CMT=Morphological transforming gene II CGO=Cytomegalovirus glycoprotein O CUL=UL 83 gene $5^{th}$ Comp=Complementary strand probe of CMT VZV—Varicella Zoster virus Showing VO=Varicella zoster ORF29 gene VDP=Varicella zoster DNA polymerase: NC membrane hybridized with contents of tube labeled NC. HSV-Nylon membrane hybridized with amplicon obtained from tube No. 1; CMV-Nylon membrane hybridized with amplicon from tube No. 2 and VZV-Nylon membrane hybridized with contents of tube No. 3

Example 6

A multiplex PCR was carried out with primer sets 10, 11, 12, 18, 19, 20, 21 and 22 which can amplify 16s ribosomal RNA gene set I and II of eubacterial genome, 16s ribosomal RNA gene of Gram-positive, 28s RNA gene from all fungi, 16s ribosomal RNA gene of Propionibacterium acnes, gyr B gene, aconitate hydratase gene and ribonuclease gene of gram-negative bacteria. The PCR mix contained 10 to 20 pmoles each of the forward and reverse primers, 200 µM of each d-ATP, d-UTP, d-CTP and d-GTP, 2 units of Taq polymerase in 50 mM Tris-HCl pH 7.5, 5 mM $MgCl_2$, 5 mM KCl, 1% bovine serum albumin, 1 mM EDTA and 1 unit of UDP glycosylase to prevent amplicon contamination. The cycling conditions are being incubation at 37° C. for 30 minutes for complete digestion of any amplicon contaminants, a denaturing step of 94° C. for 5 minutes, followed by 40 cycles of 45 seconds at 60° C., 45 seconds at 72° C. and 45 seconds at 94° C. followed by 10 minutes extension of the reaction at 72° C. Five tubes of the PCR mix mentioned above were incubated with the following DNA preparations where in the tube NC did not received any DNA tube no 1 received 5 fg of DNA from E. coli, tube 2 received 10 fg of S. aureus DNA, tube 3 received 10 fg of P. acnes DNA and tube 4 received 10 fg of C. albicans DNA. FIG. 7 shows five nylon membranes each spotted with 100 p moles of targets with SEQ ID No. 76, 77, 78, 84, 85, 86, 87 and 88 in 0.26 N NaOH. The membrane was then blocked using 2×SSPE containing 0.1% SDS and 1% BSA for one hour at 37° C. The amplicons were heated to 95° C. for 10 mins and mixed in 2×SSPE containing 0.1% SDS and hybridized for 2 hours at 52° C. After hybridization the membrane was washed five times for three minutes each in 1×SSPE containing 0.1% SDS. The membrane was incubated with Streptavidin peroxidase conjugate in 0.1 M Tris-HCl pH 7.4 containing 1% BSA, 150 mM NaCl and 0.3% tween-20. After 30 minutes at 37° C. the membrane was washed five times three minutes each with the same buffer. For development of color, the membrane was incubated for 10 minutes at 37° C. with 0.5 mg of Diaminobenzidine HCl per ml of phosphate buffered saline. The appearance of brown colored spots indicate the presence of specific pathogen.

A macro-array spotted on nylon membranes hybridized with amplicons from a multiplex PCR for identification of infectious endophthalmtis especially genomes of eubacteria, gram+ve, gram−ve, P. acnes and fungi.

Example 7

Vitreous fluid collected at autopsy from 11 AIDS patients who presented as uveitis/retinitis before death were subjected to test on multiplex PCR followed by identification of amplicon on macroarray. DNA was extracted using QIAGEN DNA purification kits from 100 µl of each vitreous sample. The DNA was reconstituted in 50 µl of the elution buffer. A multiplex PCR was carried out with primer sets 1 to 23 which can amplify all the 23 genes of, Herpes simplex virus 1 & 2 glycoprotein D, Herpes simplex virus 1 & 2 UL 44 gene, Herpes simplex virus 1 & 2 DNA polymerase gene, Cytomegalovirus Glycoprotein O gene, Cytomegalovirus Morphological transformation gene, Cytomegalovirus UL 88 gene, Varicella zoster ORF 29, Varicella zoster DNA polymerase gene, Adenoviruses Hexon Gene, Eubacterial 16s ribosomal RNA gene I, Eubacterial 16s ribosomal RNA gene region II, Gram+ve bacterial specific portion of 16s ribosomal RNA gene, Mycobacterium tuberculosis MPB 64 gene, Mycobacterium fortuitum 16s-23s RNA gene, Mycobacterium chelonae 16s-23 s RNA gene, Toxoplasma gondii B 1 gene, Chlamydia trachomatis polymorphic protein II, Fungal specific portion of 28s ribosomal RNA gene, Propionibacterium acnes specific portion of 16s-23s ribosomal RNA gene, Gram−ve bacterial specific portion of gyr B gene, gram−ve bacterial aconitate hydratase gene, Gram−ve ribonuclease I gene The PCR mix contained 10 to 20 pmoles each of the forward and reverse primers, 200 µM of each d-ATP, d-UTP, d-CTP and d-GTP, 2 units of Taq polymerase in 10 mM Tris-HCl pH 9.0, 1.5 mM $MgCl_2$, 5 mM KCl, 0.01% gelatin, 1 mM EDTA and 1 unit of UDP glycosylase to prevent amplicon contamination and 10 µl of the DNA extracted from the sample. The cycling conditions are being incubation at 37° C. for 30 minutes for complete digestion of any amplicon contaminants, two minutes at 50° C. and a denaturing step of 94° C. for 5 minutes, followed by 40 cycles of 45 seconds at 60° C., 45 seconds at 72° C. and 45 seconds at 94° C. followed by 10 minutes extension of the reaction at 72° C.

The PCR was conducted as described above with 23 sets of primers comprising sequence ID No 1-46 at a concentration of 10-20 p moles/50 µl reaction mix. The PCR products of all samples were subjected to hybridization on membranes nylon spotted with probes of SEQ ID No. 47-71. Nylon membranes were each spotted with 100 p moles of targets with SEQ ID No. 67-88 in 0.26 N NaOH. The membranes was then blocked using 2×SSPE containing 0.1% SDS and 1% BSA for one hour at 37° C. The amplicons were heated to 95° C. for 10 mins and mixed in 2×SSPE containing 0.1% SDS and hybridized for 2 hours at 52° C. After hybridization the membrane was washed five times for three minutes each in 1×SSPE containing 0.1% SDS. The membrane was incubated with Streptavidin peroxidase conjugate in 0.1 M Tris-HCl pH 7.4 containing 1% BSA, 150 mM NaCl and 0.3% tween-20. After 30 minutes at 37° C. the membrane was washed five times three minutes each with the same buffer. For development of color, the membrane was incubated for 10 minutes at 37° C. with 0.5 mg of Diaminobenzidine HCl per ml of phosphate buffered saline. The appearance of brown colored spots indicate the presence of specific pathogen.

The results obtained are summarized in Table 1. All 11 samples were identified as HSV retinitis and Uveitis by *Mycobacterium tuberculosis* while 10 of them in addition had *Toxoplasma gondii* in vitreous. The Multiplex PCR and DNA macro-array accurately identified all samples.

TABLE 1

Results of the simultaneous detection and discrimination of pathogens using multiplex PCR and hybridization on macro-array carried out on 11 autopsy samples vitreous fluid collected from AIDS patients

| Sample Identification No. | Organisms positive |
|---|---|
| A/39/06 | HSV, *Mycobacterium tuberculosis, Toxoplasma* |
| A/40/06 | HSV, *Mycobacterium tuberculosis, Toxoplasma* |
| A/05/06 | HSV, *Mycobacterium tuberculosis, Toxoplasma* |
| A/12/06 | HSV, *Mycobacterium tuberculosis, Toxoplasma* |
| A/36/06 | HSV, *Mycobacterium tuberculosis, Toxoplasma* |
| A/38/05 | HSV, *Mycobacterium tuberculosis, Toxoplasma* |
| A/14/06 | HSV, *Mycobacterium tuberculosis, Toxoplasma* |
| A/42/05 | HSV, *Mycobacterium tuberculosis, Toxoplasma* |
| A/43/05 | HSV, *Mycobacterium tuberculosis, Toxoplasma* |
| A/49/05 | HSV, TB |

Example 8

Six CSF samples collected at autopsy from AIDS patients were tested on a multiplex PC followed by macroarray. The cause of death was ascertained to be Central nervous system infection. The DNA extracted from 200 µl of samples using commercially available QIAGEN DNA extraction kits. The DNA was reconstituted in 50 µl of elution buffer. A multiplex PCR was carried out with primer sets 1 to 23 which can amplify all the 23 genes of Herpes simplex virus 1 & 2 glycoprotein D, Herpes simplex virus 1 & 2 UL 44 gene, Herpes simplex virus 1 & 2 DNA polymerase gene, Cytomegalovirus Glycoprotein O gene, Cytomegalovirus Morphological transformation gene, Cytomegalovirus UL 88 gene, Varicella zoster ORF 29, Varicella zoster DNA polymerase gene, Adenoviruses Hexon Gene, Eubacterial 16s ribosomal RNA gene I, Eubacterial 16s ribosomal RNA gene region II, Gram+ve bacterial specific portion of 16s ribosomal RNA gene, *Mycobacterium tuberculosis* MPB 64 gene, *Mycobacterium fortuitum* 16s-23s RNA gene, *Mycobacterium chelonei* 16s-23 s RNA gene, *Toxoplasma gondii* B 1 gene, *Chlamydia trachomatis* polymorphic protein II, Fungal specific portion of 28s ribosomal RNA gene, Propionibacterium acnes specific portion of 16s-23s ribosomal RNA gene, Gram−ve bacterial specific portion of gyr B gene, gram−ve bacterial aconitate hydratase gene, Gram−ve ribonuclease 1 gene.

The PCR mix contained 10 to 20 pmoles each of the forward and reverse primers, 200 µM of each d-ATP, d-UTP, d-CTP and d-GTP, 2 units of Taq polymerase in 10 mM Tris-HCl pH 9.0, 1.5 mM $MgCl_2$, 5 mM KCl, 0.01% gelatin, 1 mM EDTA and 1 unit of UDP glycosylase to prevent amplicon contamination and 10 µl of the DNA extracted from the sample. The cycling conditions are being incubation at 37° C. for 30 minutes for complete digestion of any amplicon contaminants, two minutes at 50° C. and a denaturing step of 94° C. for 5 minutes, followed by 40 cycles of 45 seconds at 60° C., 45 seconds at 72° C. and 45 seconds at 94° C. followed by 10 minutes extension of the reaction at 72° C. The PCR was conducted as described above with 23 sets of primers comprising sequence ID Nos 1-46 at a concentration of 10-20 p moles/50 µl reaction mix. The PCR products of all samples were subjected to hybridization on nylon membranes spotted with 100 p moles of targets SEQ ID No. 67-88 in 0.26 N NaOH. The membrane was then blocked using 2×SSPE containing 0.1% SDS and 1% BSA for one hour at 37° C. The amplicons were heated to 95° C. for 10 mins and mixed in 2×SSPE containing 0.1% SDS and hybridized for 2 hours at 52° C. After hybridization the membrane was washed five times for three minutes each in 1×SSPE containing 0.1% SDS. The membrane was incubated with Streptavidin peroxidase conjugate in 0.1 M Tris-HCl pH 7.4 containing 1% BSA, 150 mM NaCl and 0.3% tween-20. After 30 minutes at 37° C. the membrane was washed five times three minutes each with the same buffer. For development of color, the membrane was incubated for 10 minutes at 37° C. with 0.5 mg of Diaminobenzidine HCl per ml of phosphate buffered saline. The appearance of brown colored spots indicate the presence of specific pathogen.

TABLE 2

Results of the simultaneous detection and discrimination of pathogens using multiplex PCR and hybridization on macro-array carried out on six autopsy samples of CSF collected from AIDS patients

| SAMPLE DIAGNOSIS | No. Tested | No. Positive |
|---|---|---|
| HSV Encephalitis | 4 | 4 |
| CMV Encephalitis | 2 | 2 |
| VZV Encephalitis | 2 | 2 |
| *Toxoplasma* encephalitis | 3 | 3 |
| Tuberculous meningitis | 3 | 3 |

Example 9

A series of 19 ocular specimen either aqueous humor or vitreous fluid were obtained with various clinical diagnoses. From about 50-100 µl sample DNA was extracted using commercially available DNA extraction kits and the DNA was reconstituted in 50 µl of water and 10 µl was used for multiplex PCR containing 10 p 20 p moles each of primer sets 1-23 comprising of SEQ ID No 1-46. The PCR reagent composition and the thermal cycling conditions are the same as described in example 6 & 7 above. The amplicon was hybridized with targets with SEQ ID No 67-88 as described in the above example. The results are summarized below which demonstrates the clinical utility of the primer sets and probes.

TABLE 3

Results of the simultaneous detection and discrimination of pathogens using multiplex PCR and hybridization on macro-array carried out on ocular samples of aqueous humor and vitreous fluid collected from patients.

| Sample No | Clinical Diagnosis | Result |
|---|---|---|
| 1 | Viral Retinitis | CMV |
| 2 | Viral retinitis and Uveities | *M. tiuberculosis, M. chelonae* and VZV |
| 3 | Infectious Endopthalmitis | Eubacterial & Gram-positive |
| 4 | Viral Retinitis | HSV |
| 5 | Infectious Endophthalmitis | Eubacterial & Gram-positive |
| 6 | Infectious Endophthalmitis | Eubacterial & Gram-positive |
| 7 | Infectious Endophthalmitis | Eubacterial & Gram-positive |
| 8 | Infectious Endophthalmitis | Eubacterial & Gram-positive |
| 9 | Infectious Endophthalmitis | Eubacterial & Gram-positive |
| 10 | Infectious Endophthalmitis | Eubacterial & Gram-positive |
| 11 | Infectious Endophthalmitis and Uveities | Fungal infection |
| 12 | Infectious Endophthalmitis and Uveities | Negative |
| 13 | Infectious Endophthalmitis | *Propionibacterium acnes* |
| 14 | Infectious Endophthalmitis | Eubacterial & Gram-positive |
| 15 | Infectious Endophthalmitis | Eubacterial & Gram-positive |
| 16 | Infectious Endophthalmitis and Uveities | Eubacterial & *M. tuberculosis* |
| 17 | Infectious Endophthalmitis | Eubacterial &-Gram-positive |
| 18 | Infectious Endophthalmitis | Negative |
| 19 | Infectious Endophthalmitis | Eubacterial & Gram-positive |

Advantages

1. Highly efficient and time saving kit.
2. Identification of specific pathogen at very early stage of infection will help the physician to select the appropriate treatment regimen for spread of the disease and its cure.
3. Identification of multiple infections from the same samples will also be useful for a treatment using combination of drugs for effective therapy.

We claim:

1. A method for the detection of pathogens in a sample comprising the steps of: amplifying specific genes of the pathogens by performing multiplex PCR (polymerase chain reaction) assay using the primer set 1 ((SEQ ID NO:1) and (SEQ ID NO:2)), set 2 ((SEQ ID NO:3) and (SEQ ID NO:4)), set 3 ((SEQ ID NO:5) and (SEQ ID NO:6)), set 4 ((SEQ ID NO:7) and (SEQ ID NO:8)), set 5 ((SEQ ID NO:9) and (SEQ ID NO:10)), set 6 ((SEQ ID NO: 11) and (SEQ ID NO:12)), set 7 ((SEQ ID NO:13) and (SEQ ID NO:14)) and set 8 ((SEQ ID NO:15) and (SEQ ID NO:16)), set 13 ((SEQ ID NO: 25) and (SEQ ID NO:26)), set 16 ((SEQ ID NO: 31) and (SEQ ID NO: 32)) and set 18 ((SEQ ID NO: 35) and (SEQ ID NO: 36)); hybridizing the amplified products (probes) to complementary DNA sequences (targets) immobilized on a solid phase matrix in a multiplex format, and detecting the hybridized products, wherein the pathogens are selected from the group consisting of Herpes simplex viruses 1 and 2, cytomegaloviruses, Varicella Zoster virus, Adenoviruses, Eubacteria, Gram positive bacteria, Gram negative bacteria, Fungi, *Mycobacterium tuberculosis, Mycobacterium chelonei, Mycobacterium fortuitum, Toxoplasma gondii* and *Chlamydia trachomatis*.

2. A method for detection and discrimination of two or more groups of pathogens comprising the steps of
    a) performing multiplex PCR (polymerase chain reaction) on DNA from a clinical sample using the combination of primer sets 1 to 22 (SEQ ID NO:1 to SEQ ID NO: 44) to obtain amplified PCR products,
    b) denaturing the amplified PCR products,
    c) hybridizing the denatured amplified PCR products with target DNA sequences, and
    d) identifying the pathogens by detecting for hybridization.

3. The method as claimed in claim 2, wherein the pathogen is known to cause a syndrome selected from the group consisting of infectious endophthalmitis, keratitis, uveitis, retinitis, meningitis, ocular infection, and meningoencephalitis.

4. The method as claimed in claim 2, wherein the target DNA sequences are selected from the group consisting of SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88.

5. The method as claimed in claim 3, wherein primer sets 1 to 22 (SEQ ID NO.:1 to SEQ ID No: 44) are used together in a reaction vessel at uniform thermal-cycling conditions comprising a denaturing step of 94 C for 5 minutes, followed by 40 cycles of 45 seconds at 60° C.-64° C., 45 seconds at 72° C. for 45 seconds at 94° C. followed by 10 minutes extension of the reaction at 72° C.

6. The method as claimed in claim 2, wherein said primers are labeled at 5' end using a biotin moiety resulting in detection by formation of coloured product; or wherein the primers are labeled by fluorescent labels selected from organic fluorescent labels selected from a group consisting of Fluorescene isothiocyanate FITC, and inorganic fluorescent nanoparticles, Quantum Dots™, Cy3, and Cy5 enabling detection by any fluorescent scanning device or microscopy.

7. The method as claimed in claim 2, wherein the hybridization is detected using amplified PCR products comprising sequences selected from the group consisting of SED ID NO:45 to SEQ ID NO:66 as probes in a macroarray, slot blot or line probe assay.

8. The method as claimed in claim 7, wherein the macroarray comprises target DNA sequences SEQ ID NO:67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88 fixed to a solid phase selected from nitrocellulose, nylon, charged nylon, glass and polystyrene or a combination thereof.

9. The method according to claim 2, wherein the sample is selected from the group consisting of aqueous humor, vitreous fluid, vitreous lavage, corneal scrapings, conjunctival swabs, Cerebro-spinal fluid, blood, and plasma.

* * * * *

UNITED STATES PATENT AND TRADEMARK OFFICE
CERTIFICATE OF CORRECTION

PATENT NO. : 8,465,951 B2  
APPLICATION NO. : 12/602564  
DATED : June 18, 2013  
INVENTOR(S) : Rao et al.

Page 1 of 1

It is certified that error appears in the above-identified patent and that said Letters Patent is hereby corrected as shown below:

In the Specification

Column 10, line 58, "23" should be changed to --22--.

Column 12, line 51, "17" should be changed to --16--; line 55, "18" should be changed to --17--; line 59, "19" should be changed to --18--; line 64, "20" should be changed to --19--.

Column 13, line 2, "21" should be changed to --20--; line 7, "22" should be changed to --21--; line 11, "23" should be changed to --22--; line 15, "67" should be changed to --66--.

Column 18, line 41, "18" should be changed to --17--.

Column 22, line 43, "23" should be changed to --22--; line 44, "23" should be changed to --22--.

Column 23, line 7, "23" should be changed to --22--; line 8, "46" should be changed to --44--; line 11, "47-71" should be changed to --45-66--; line 60, "23" should be changed to --22--; line 61, "23" should be changed to --22--.

Column 24, line 24, "23" should be changed to --22--; line 25, "46" should be changed to --44--; line 66, "23" should be changed to --22--; line 67, "46" should be changed to --44--.

Signed and Sealed this  
Twenty-eighth Day of January, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,465,951 B2 | Page 1 of 1 |
| APPLICATION NO. | : 12/602564 | |
| DATED | : June 18, 2013 | |
| INVENTOR(S) | : Rao et al. | |

It is certified that error appears in the above-identified patent and that said Letters Patent is hereby corrected as shown below:

In the Specification

Column 15, line 46, "67-91" should be changed to --45-66--.

Signed and Sealed this
Thirteenth Day of May, 2014

Michelle K. Lee
*Deputy Director of the United States Patent and Trademark Office*

SEQUENCE LISTING

<160> NUMBER OF SEQ ID NOS: 88

<210> SEQ ID NO 1
<211> LENGTH: 20
<212> TYPE: DNA
<213> ORGANISM: Artificial Sequence
<220> FEATURE:
<223> OTHER INFORMATION: forward primer for Herpes simplex virus
      glycoprotein D gene

<400> SEQUENCE: 1
cgcttggttt cggatgggag                                                   20

<210> SEQ ID NO 2
<211> LENGTH: 22
<212> TYPE: DNA
<213> ORGANISM: Artificial Sequence
<220> FEATURE:
<223> OTHER INFORMATION: reverse primer for Herpes simplex virus
      glycoprotein D gene

<400> SEQUENCE: 2
gcccccagag acttgttgta gg                                                22

<210> SEQ ID NO 3
<211> LENGTH: 21
<212> TYPE: DNA
<213> ORGANISM: Artificial Sequence
<220> FEATURE:
<223> OTHER INFORMATION: forward primer for Herpes simplex virus UL 44
      gene

<400> SEQUENCE: 3
ggcaatcgtg tacgtcgtcc g                                                 21

<210> SEQ ID NO 4
<211> LENGTH: 19

```
<212> TYPE: DNA
<213> ORGANISM: Artificial Sequence
<220> FEATURE:
<223> OTHER INFORMATION: reverse primer for Herpes simplex virus UL 44
      gene

<400> SEQUENCE: 4 cggggggggtc ttgcgttac                                              19

<210> SEQ ID NO 5
<211> LENGTH: 23
<212> TYPE: DNA
<213> ORGANISM: Artificial Sequence
<220> FEATURE:
<223> OTHER INFORMATION: forward primer for Herpes simplex virus
      polymerase gene

<400> SEQUENCE: 5
caagctgacg gacatttaca agg                                          23

<210> SEQ ID NO 6
<211> LENGTH: 19
<212> TYPE: DNA
<213> ORGANISM: Artificial Sequence
<220> FEATURE:
<223> OTHER INFORMATION: reverse primer for Herpes simplex virus
      polymerase gene

<400> SEQUENCE: 6
gtcccacacg cgaaacacg                                               19

<210> SEQ ID NO 7
<211> LENGTH: 21
<212> TYPE: DNA
<213> ORGANISM: Artificial Sequence
<220> FEATURE:
<223> OTHER INFORMATION: forward primer for Cytomegalovirus glycoprotein
      O gene

<400> SEQUENCE: 7
ttccggctca tggcgttaac c                                            21

<210> SEQ ID NO 8
<211> LENGTH: 21
<212> TYPE: DNA
<213> ORGANISM: Artificial Sequence
<220> FEATURE:
<223> OTHER INFORMATION: reverse primer for Cytomegalovirus glycoprotein
      O gene

<400> SEQUENCE: 8
cgccctgctt ttacgttacg c                                            21

<210> SEQ ID NO 9
<211> LENGTH: 20
<212> TYPE: DNA
<213> ORGANISM: Artificial Sequence
<220> FEATURE:
<223> OTHER INFORMATION: forward primer for Cytomegalovirus
      morphological transformation gene

<400> SEQUENCE: 9
cggcgacgac gacgataaag                                              20

<210> SEQ ID NO 10
<211> LENGTH: 23
<212> TYPE: DNA
<213> ORGANISM: Artificial Sequence
```

```
<220> FEATURE:
<223> OTHER INFORMATION: reverse primer for Cytomegalovirus
      morphological transformation gene

<400> SEQUENCE: 10
caatctggtc gcgtaatcct ctg                                              23

<210> SEQ ID NO 11
<211> LENGTH: 19
<212> TYPE: DNA
<213> ORGANISM: Artificial Sequence
<220> FEATURE:
<223> OTHER INFORMATION: forward primer for Cytomegalovirus UL 88 gene

<400> SEQUENCE: 11
gggcacgtcc tcgcagaag                                                   19

<210> SEQ ID NO 12
<211> LENGTH: 23
<212> TYPE: DNA
<213> ORGANISM: Artificial Sequence
<220> FEATURE:
<223> OTHER INFORMATION: reverse primer for Cytomegalovirus UL 88 gene

<400> SEQUENCE: 12
ccaagatgca ggtgataggt gac                                              23

<210> SEQ ID NO 13
<211> LENGTH: 23
<212> TYPE: DNA
<213> ORGANISM: Artificial Sequence
<220> FEATURE:
<223> OTHER INFORMATION: forward primer for Varicella zoster ORF 29

<400> SEQUENCE: 13
ggtcttgccg gagctggtat tac                                              23

<210> SEQ ID NO 14
<211> LENGTH: 23
<212> TYPE: DNA
<213> ORGANISM: Artificial Sequence
<220> FEATURE:
<223> OTHER INFORMATION: reverse primer for Varicella zoster ORF 29

<400> SEQUENCE: 14
tgcctccgtg aaagacaaag aca                                              23

<210> SEQ ID NO 15
<211> LENGTH: 26
<212> TYPE: DNA
<213> ORGANISM: Artificial Sequence
<220> FEATURE:
<223> OTHER INFORMATION: forward primer for Varicella zoster DNA
      polymerase gene

<400> SEQUENCE: 15
tccatttaac gttgcatcat tttgtg                                           26

<210> SEQ ID NO 16
<211> LENGTH: 23
<212> TYPE: DNA
<213> ORGANISM: Artificial Sequence
<220> FEATURE:
<223> OTHER INFORMATION: reverse primer for Varicella zoster DNA
      polymerase gene

<400> SEQUENCE: 16
```

```
acgttccggt agcgagttat ctg                                        23

<210> SEQ ID NO 17
<211> LENGTH: 20
<212> TYPE: DNA
<213> ORGANISM: Artificial Sequence
<220> FEATURE:
<223> OTHER INFORMATION: forward primer for Adenovirus hexon gene

<400> SEQUENCE: 17
cgccgccaac atgctctacc                                            20

<210> SEQ ID NO 18
<211> LENGTH: 20
<212> TYPE: DNA
<213> ORGANISM: Artificial Sequence
<220> FEATURE:
<223> OTHER INFORMATION: reverse primer for Adenovirus hexon gene

<400> SEQUENCE: 18
gttgcgggag gggatggata                                            20

<210> SEQ ID NO 19
<211> LENGTH: 24
<212> TYPE: DNA
<213> ORGANISM: Artificial Sequence
<220> FEATURE:
<223> OTHER INFORMATION: forward primer for Eubacterial16s ribosomal RNA
      gene region I

<400> SEQUENCE: 19
tgggctacac acgtgctaca atgg                                       24

<210> SEQ ID NO 20
<211> LENGTH: 24
<212> TYPE: DNA
<213> ORGANISM: Artificial Sequence
<220> FEATURE:
<223> OTHER INFORMATION: reverse primer for Eubacterial16s ribosomal RNA
      gene region I

<400> SEQUENCE: 20
cggactacga tcggttttgt gaga                                       24

<210> SEQ ID NO 21
<211> LENGTH: 23
<212> TYPE: DNA
<213> ORGANISM: Artificial Sequence
<220> FEATURE:
<223> OTHER INFORMATION: forward primer for Eubacterial16s ribosomal RNA
      gene region II

<400> SEQUENCE: 21
ggcctaacac atgcaagtcg agc                                        23

<210> SEQ ID NO 22
<211> LENGTH: 25
<212> TYPE: DNA
<213> ORGANISM: Artificial Sequence
<220> FEATURE:
<223> OTHER INFORMATION: reverse primer for Eubacterial16s ribosomal RNA
      gene region II

<400> SEQUENCE: 22
ggcagattcc taggcattac tcacc                                      25

<210> SEQ ID NO 23
```

```
<211> LENGTH: 25
<212> TYPE: DNA
<213> ORGANISM: Artificial Sequence
<220> FEATURE:
<223> OTHER INFORMATION: forward primer for Gram +ve bacterial specific
      portion of 16a ribosomal RNA gene

<400> SEQUENCE: 23
acgtcaaatc atcatgcccc cttat                                             25

<210> SEQ ID NO 24
<211> LENGTH: 22
<212> TYPE: DNA
<213> ORGANISM: Artificial Sequence
<220> FEATURE:
<223> OTHER INFORMATION: reverse primer for Gram +ve bacterial specific
      portion of 16a ribosomal RNA gene

<400> SEQUENCE: 24 tgcagcccctt tgtaccgtcc at                                               22

<210> SEQ ID NO 25
<211> LENGTH: 20
<212> TYPE: DNA
<213> ORGANISM: Artificial Sequence
<220> FEATURE:
<223> OTHER INFORMATION: forward primer for Mycobacterium tuberculosis
      MPB 64 gene

<400> SEQUENCE: 25
gcggaacgtg ggaccaatac                                                   20

<210> SEQ ID NO 26
<211> LENGTH: 22
<212> TYPE: DNA
<213> ORGANISM: Artificial Sequence
<220> FEATURE:
<223> OTHER INFORMATION: reverse primer for Mycobacterium tuberculosis
      MPB 64 gene

<400> SEQUENCE: 26
cgacggggtg attttcttct tc                                                22

<210> SEQ ID NO 27
<211> LENGTH: 29
<212> TYPE: DNA
<213> ORGANISM: Artificial Sequence
<220> FEATURE:
<223> OTHER INFORMATION: forward primer for Mycobacterium fortuitum
      16s - 23s RNA gene

<400> SEQUENCE: 27 aactttttg actgccagac acactattg                                          29

<210> SEQ ID NO 28
<211> LENGTH: 19
<212> TYPE: DNA
<213> ORGANISM: Artificial Sequence
<220> FEATURE:
<223> OTHER INFORMATION: reverse primer for Mycobacterium fortuitum
      16s - 23s RNA gene

<400> SEQUENCE: 28
ggatgccacc ccccaaaag                                                    19

<210> SEQ ID NO 29
<211> LENGTH: 24
<212> TYPE: DNA
```

<213> ORGANISM: Artificial Sequence
<220> FEATURE:
<223> OTHER INFORMATION: forward primer for Mycobacterium chelonae
    16s - 23s RNA gene

<400> SEQUENCE: 29
tggttactcg cttggtgaat atgt                                          24

<210> SEQ ID NO 30
<211> LENGTH: 23
<212> TYPE: DNA
<213> ORGANISM: Artificial Sequence
<220> FEATURE:
<223> OTHER INFORMATION: reverse primer for Mycobacterium chelonae
    16s - 23s RNA gene

<400> SEQUENCE: 30
gacgttttgc cgactaccta tcc                                           23

<210> SEQ ID NO 31
<211> LENGTH: 21
<212> TYPE: DNA
<213> ORGANISM: Artificial Sequence
<220> FEATURE:
<223> OTHER INFORMATION: forward primer for Toxoplasma gondii B1 gene

<400> SEQUENCE: 31
cccctctgct ggcgaaaagt g                                             21

<210> SEQ ID NO 32
<211> LENGTH: 22
<212> TYPE: DNA
<213> ORGANISM: Artificial Sequence
<220> FEATURE:
<223> OTHER INFORMATION: reverse primer for Toxoplasma gondii B1 gene

<400> SEQUENCE: 32
ggcgaccaat ctgcgaatac ac                                            22

<210> SEQ ID NO 33
<211> LENGTH: 24
<212> TYPE: DNA
<213> ORGANISM: Artificial Sequence
<220> FEATURE:
<223> OTHER INFORMATION: forward primer for Chlamydia trachomatis
    polymorphic protein II

<400> SEQUENCE: 33
aatcgtatct cgggttaatg ttgc                                          24

<210> SEQ ID NO 34
<211> LENGTH: 23
<212> TYPE: DNA
<213> ORGANISM: Artificial Sequence
<220> FEATURE:
<223> OTHER INFORMATION: reverse primer for Chlamydia trachomatis
    polymorphic protein II

<400> SEQUENCE: 34
tcgaggaaaa ccgtatgaga aac                                           23

<210> SEQ ID NO 35
<211> LENGTH: 21
<212> TYPE: DNA
<213> ORGANISM: Artificial Sequence
<220> FEATURE:
<223> OTHER INFORMATION: forward primer for fungal specific portion of
    28a ribosomal RNA gene -continued

<400> SEQUENCE: 35
gctgggactg aggactgcga c                                              21

<210> SEQ ID NO 36
<211> LENGTH: 22
<212> TYPE: DNA
<213> ORGANISM: Artificial Sequence
<220> FEATURE:
<223> OTHER INFORMATION: reverse primer for fungal specific portion of
     28a ribosomal RNA gene

<400> SEQUENCE: 36
ttcaagacgg gcggcatata ac                                             22

<210> SEQ ID NO 37
<211> LENGTH: 20
<212> TYPE: DNA
<213> ORGANISM: Artificial Sequence
<220> FEATURE:
<223> OTHER INFORMATION: forward primer for Propionibacterium acnes
     specific portion of 16s-23 ribosomal RNA gene

<400> SEQUENCE: 37
tggcgaacgg gtgagtaaca                                                20

<210> SEQ ID NO 38
<211> LENGTH: 21
<212> TYPE: DNA
<213> ORGANISM: Artificial Sequence
<220> FEATURE:
<223> OTHER INFORMATION: reverse primer for Propionibacterium acnes
     specific portion of 16s-23 ribosomal RNA gene

<400> SEQUENCE: 38
ccggtattag ccccagtttc c                                              21

<210> SEQ ID NO 39
<211> LENGTH: 19
<212> TYPE: DNA
<213> ORGANISM: Artificial Sequence
<220> FEATURE:
<223> OTHER INFORMATION: forward primer for Gram -ve bacterial specific
     portion of gyr B gene

<400> SEQUENCE: 39
cggcggcaag ttcgacgac                                                 19

<210> SEQ ID NO 40
<211> LENGTH: 19
<212> TYPE: DNA
<213> ORGANISM: Artificial Sequence
<220> FEATURE:
<223> OTHER INFORMATION: reverse primer for Gram -ve bacterial specific
     portion of gyr B gene

<400> SEQUENCE: 40
ccaccgagac gcccacacc                                                 19

<210> SEQ ID NO 41
<211> LENGTH: 18
<212> TYPE: DNA
<213> ORGANISM: Artificial Sequence
<220> FEATURE:
<223> OTHER INFORMATION: forward primer for Gram -ve bacterial aconitate
     hydratase gene

<400> SEQUENCE: 41

```
ccaggtcggc ggagaagc                                                   18
```

<210> SEQ ID NO 42
<211> LENGTH: 17
<212> TYPE: DNA
<213> ORGANISM: Artificial Sequence
<220> FEATURE:
<223> OTHER INFORMATION: reverse primer for Gram -ve bacterial aconitate
      hydratase gene

<400> SEQUENCE: 42

```
ccaccggccc gatgacc                                                    17
```

<210> SEQ ID NO 43
<211> LENGTH: 18
<212> TYPE: DNA
<213> ORGANISM: Artificial Sequence
<220> FEATURE:
<223> OTHER INFORMATION: forward primer for Gram -ve bacterial
      ribonuclease 1 gene

<400> SEQUENCE: 43

```
gccgccctga ccaccttc                                                   18
```

<210> SEQ ID NO 44
<211> LENGTH: 19
<212> TYPE: DNA
<213> ORGANISM: Artificial Sequence
<220> FEATURE:
<223> OTHER INFORMATION: reverse primer for Gram -ve bacterial
      ribonuclease 1 gene

<400> SEQUENCE: 44

```
gcgggttgtt cggcatcag                                                  19
```

<210> SEQ ID NO 45
<211> LENGTH: 87
<212> TYPE: DNA
<213> ORGANISM: Artificial Sequence
<220> FEATURE:
<223> OTHER INFORMATION: probe for Herpes simplex virus glycoprotein D
      gene

<400> SEQUENCE: 45

```
cgcttggttt cggatgggag gcaactgtgc tatccccatc acggtcatgg agtacaccga     60
atgctcctac aacaagtctc tgggggc                                         87
```

<210> SEQ ID NO 46
<211> LENGTH: 70
<212> TYPE: DNA
<213> ORGANISM: Artificial Sequence
<220> FEATURE:
<223> OTHER INFORMATION: probe for Herpes simplex virus UL 44 gene

<400> SEQUENCE: 46

```
ggcaatcgtg tacgtcgtcc gcacatcaca gtcgcggcag cgtcatcggc ggtaacgcaa     60
gaccccccg                                                             70
```

<210> SEQ ID NO 47
<211> LENGTH: 79
<212> TYPE: DNA
<213> ORGANISM: Artificial Sequence
<220> FEATURE:
<223> OTHER INFORMATION: probe for Herpes simplex virus polymerase gene

<400> SEQUENCE: 47

```
caagctgacg gacatttaca aggtccccct ggacgggtac ggccgcatga acggccgggg    60
cgtgtttcgc gtgtgggac                                                 79

<210> SEQ ID NO 48
<211> LENGTH: 72
<212> TYPE: DNA
<213> ORGANISM: Artificial Sequence
<220> FEATURE:
<223> OTHER INFORMATION: probe for Cytomegalovirus glycoprotein O gene

<400> SEQUENCE: 48
ttccggctca tgcgttaac caggtagaaa ctgtgtgtac agttgcgttg tgcgtaacgt    60
aaaagcaggg cg                                                        72

<210> SEQ ID NO 49
<211> LENGTH: 65
<212> TYPE: DNA
<213> ORGANISM: Artificial Sequence
<220> FEATURE:
<223> OTHER INFORMATION: probe for Cytomegalovirus morphological
      transformation gene

<400> SEQUENCE: 49
cggcgacgac gacgataaag aatacaaagc cgcagtgtcg tccagaggat tacgcgacca    60
gattg                                                                65

<210> SEQ ID NO 50
<211> LENGTH: 68
<212> TYPE: DNA
<213> ORGANISM: Artificial Sequence
<220> FEATURE:
<223> OTHER INFORMATION: probe for Cytomegalovirus UL 88 gene

<400> SEQUENCE: 50
gggcacgtcc tcgcagaagg actccaggta caccttgacg tactggtcac ctatcacctg    60
catcttgg                                                             68

<210> SEQ ID NO 51
<211> LENGTH: 79
<212> TYPE: DNA
<213> ORGANISM: Artificial Sequence
<220> FEATURE:
<223> OTHER INFORMATION: probe for Varicella zoster ORF 29

<400> SEQUENCE: 51
ggtcttgccg gagctggtat taccttaaaa ctcactacca gtcatttcta tccatctgtc    60
tttgtctttc acggaggca                                                 79

<210> SEQ ID NO 52
<211> LENGTH: 85
<212> TYPE: DNA
<213> ORGANISM: Artificial Sequence
<220> FEATURE:
<223> OTHER INFORMATION: probe for Varicella zoster DNA polymerase gene

<400> SEQUENCE: 52
tccatttaac gttgcatcat tttgtgttat catagaactg cgtaaacact cggcaagtaa    60
tacagataac tcgctaccgg aacgt                                          85

<210> SEQ ID NO 53
<211> LENGTH: 70
<212> TYPE: DNA
```

```
<213> ORGANISM: Artificial Sequence
<220> FEATURE:
<223> OTHER INFORMATION: probe for Adenovirus hexon gene

<400> SEQUENCE: 53
cgccgccaac atgctctacc ctatacccgc caacgctacc aacgtgccca tatccatccc      60
ctcccgcaac                                                            70

<210> SEQ ID NO 54
<211> LENGTH: 86
<212> TYPE: DNA
<213> ORGANISM: Artificial Sequence
<220> FEATURE:
<223> OTHER INFORMATION: probe for Eubacterial16s ribosomal RNA gene
      region I

<400> SEQUENCE: 54
tgggctacac acgtgctaca atggtcggta cagagggtcg ccaaaccgcg aggtggagct      60
aatctcacaa aaccgatcgt agtccg                                          86

<210> SEQ ID NO 55
<211> LENGTH: 86
<212> TYPE: DNA
<213> ORGANISM: Artificial Sequence
<220> FEATURE:
<223> OTHER INFORMATION: probe for Eubacterial16s ribosomal RNA gene
      region II

<400> SEQUENCE: 55
ggcctaacac atgcaagtcg agcggatgaa aggagcttgc tcctggattc agcggcggac      60
gggtgagtaa tgcctaggaa tctgcc                                          86

<210> SEQ ID NO 56
<211> LENGTH: 71
<212> TYPE: DNA
<213> ORGANISM: Artificial Sequence
<220> FEATURE:
<223> OTHER INFORMATION: probe for Gram +ve bacterial specific portion
      of 16a ribosomal RNA gene

<400> SEQUENCE: 56
acgtcaaatc atcatgcccc cttatgacct gggctacaca cgtgctacaa tggacggtac     60
aaagggctgc a                                                          71

<210> SEQ ID NO 57
<211> LENGTH: 84
<212> TYPE: DNA
<213> ORGANISM: Artificial Sequence
<220> FEATURE:
<223> OTHER INFORMATION: probe for Mycobacterium tuberculosis MPB 64
      gene

<400> SEQUENCE: 57
gcggaacgtg ggaccaatac ctgggttggg ccggctgctt cgggcagcaa ctcccccggg     60
ttgaagaaga aaatcacccc gtcg                                            84

<210> SEQ ID NO 58
<211> LENGTH: 74
<212> TYPE: DNA
<213> ORGANISM: Artificial Sequence
<220> FEATURE:
<223> OTHER INFORMATION: probe for Mycobacterium fortuitum 16s - 23s RNA
      gene

<400> SEQUENCE: 58
```

```
aacttttttg actgccagac acactattgg gctttgagac aacaggcccg tgcccctttt    60 gggggtggc atcc                                                       74
```

<210> SEQ ID NO 59
<211> LENGTH: 70
<212> TYPE: DNA
<213> ORGANISM: Artificial Sequence
<220> FEATURE:
<223> OTHER INFORMATION: probe for Mycobacterium chelonae 16s - 23s RNA
      gene

<400> SEQUENCE: 59

```
tggttactcg cttggtgaat atgttttata aatcctgtcc accccgtgga taggtagtcg    60
gcaaaacgtc                                                           70
```

<210> SEQ ID NO 60
<211> LENGTH: 70
<212> TYPE: DNA
<213> ORGANISM: Artificial Sequence
<220> FEATURE:
<223> OTHER INFORMATION: probe for Toxoplasma gondii B1 gene

<400> SEQUENCE: 60

```
cccctctgct ggcgaaaagt gaaattcatg agtatctgtg caactttggt gtattcgcag    60
attggtcgcc                                                           70
```

<210> SEQ ID NO 61
<211> LENGTH: 79
<212> TYPE: DNA
<213> ORGANISM: Artificial Sequence
<220> FEATURE:
<223> OTHER INFORMATION: probe for Chlamydia trachomatis polymorphic
      protein II

<400> SEQUENCE: 61

```
aatcgtatct cgggttaatg ttgcatgatg ctttatcaaa tgacaagctt agatccgttt    60
ctcatacggt tttcctcga                                                 79
```

<210> SEQ ID NO 62
<211> LENGTH: 68
<212> TYPE: DNA
<213> ORGANISM: Artificial Sequence
<220> FEATURE:
<223> OTHER INFORMATION: probe for fungal specific portion of 28a
      ribosomal RNA gene

<400> SEQUENCE: 62

```
gctgggactg aggactgcga cgtaagtcaa ggatgctggc ataatggtta tatgccgccc    60
gtcttgaa                                                             68
```

<210> SEQ ID NO 63
<211> LENGTH: 77
<212> TYPE: DNA
<213> ORGANISM: Artificial Sequence
<220> FEATURE:
<223> OTHER INFORMATION: probe for Propionibacterium acnes specific
      portion of 16s-23 ribosomal RNA gene

<400> SEQUENCE: 63

```
tggcgaacgg gtgagtaaca cgtgagtaac ctgcccttga ctttgggata acttcaggaa    60
actggggcta ataccgg                                                   77
```

```
<210> SEQ ID NO 64
<211> LENGTH: 68
<212> TYPE: DNA
<213> ORGANISM: Artificial Sequence
<220> FEATURE:
<223> OTHER INFORMATION: probe for Gram -ve bacterial specific portion
      of gyr B gene

<400> SEQUENCE: 64
cggcggcaag ttcgacgaca acacctacaa ggtgtccggc ggcttgcacg gtgtgggcgt    60
ctcggtgg                                                             68

<210> SEQ ID NO 65
<211> LENGTH: 66
<212> TYPE: DNA
<213> ORGANISM: Artificial Sequence
<220> FEATURE:
<223> OTHER INFORMATION: probe for Gram -ve bacterial aconitate
      hydratase gene

<400> SEQUENCE: 65
ccaggtcggc ggagaagccg aggcaggcga ggtccttcag ttcgtcgcgg gtcatcgggc    60
cggtgg                                                               66

<210> SEQ ID NO 66
<211> LENGTH: 64
<212> TYPE: DNA
<213> ORGANISM: Artificial Sequence
<220> FEATURE:
<223> OTHER INFORMATION: probe for Gram -ve bacterial ribonuclease 1
      gene

<400> SEQUENCE: 66
gccgccctga ccaccttcat cagcctggcc ggccgttacc tggtgctgat gccgaacaac    60
ccgc                                                                 64

<210> SEQ ID NO 67
<211> LENGTH: 45
<212> TYPE: DNA
<213> ORGANISM: Artificial Sequence
<220> FEATURE:
<223> OTHER INFORMATION: probe for Herpes simplex virus glycoprotein D
      gene

<400> SEQUENCE: 67
gcaactgtgc tatccccatc acggtcatgg agtacaccga atgct                    45

<210> SEQ ID NO 68
<211> LENGTH: 30
<212> TYPE: DNA
<213> ORGANISM: Artificial Sequence
<220> FEATURE:
<223> OTHER INFORMATION: target for Herpes simplex virus UL 44 gene

<400> SEQUENCE: 68
cacatcacag tcgcggcagc gtcatcggcg                                     30

<210> SEQ ID NO 69
<211> LENGTH: 37
<212> TYPE: DNA
<213> ORGANISM: Artificial Sequence
<220> FEATURE:
<223> OTHER INFORMATION: target for Herpes simplex virus polymerase gene

<400> SEQUENCE: 69 tcccccctgga cgggtacggc cgcatgaacg gccgggg                            37
```

<210> SEQ ID NO 70
<211> LENGTH: 31
<212> TYPE: DNA
<213> ORGANISM: Artificial Sequence
<220> FEATURE:
<223> OTHER INFORMATION: target for Cytomegalovirus glycoprotein O gene

<400> SEQUENCE: 70
aggtagaaac tgtgtgtaca gttgcgttgt g                                  31

<210> SEQ ID NO 71
<211> LENGTH: 22
<212> TYPE: DNA
<213> ORGANISM: Artificial Sequence
<220> FEATURE:
<223> OTHER INFORMATION: target for Cytomegalovirus morphological
      transformation gene

<400> SEQUENCE: 71
aatacaaagc cgcagtgtcg tc                                            22

<210> SEQ ID NO 72
<211> LENGTH: 26
<212> TYPE: DNA
<213> ORGANISM: Artificial Sequence
<220> FEATURE:
<223> OTHER INFORMATION: target for Cytomegalovirus UL 88 gene

<400> SEQUENCE: 72
gactccaggt acaccttgac gtactg                                        26

<210> SEQ ID NO 73
<211> LENGTH: 33
<212> TYPE: DNA
<213> ORGANISM: Artificial Sequence
<220> FEATURE:
<223> OTHER INFORMATION: target for Varicella zoster ORF 29

<400> SEQUENCE: 73
cttaaaactc actaccagtc atttctatcc atc                                33

<210> SEQ ID NO 74
<211> LENGTH: 36
<212> TYPE: DNA
<213> ORGANISM: Artificial Sequence
<220> FEATURE:
<223> OTHER INFORMATION: target for Varicella zoster DNA polymerase gene

<400> SEQUENCE: 74
ttatcataga actgcgtaaa cactcggcaa gtaata                             36

<210> SEQ ID NO 75
<211> LENGTH: 30
<212> TYPE: DNA
<213> ORGANISM: Artificial Sequence
<220> FEATURE:
<223> OTHER INFORMATION: target for Adenovirus hexon gene

<400> SEQUENCE: 75
ctatacccgc caacgctacc aacgtgccca                                    30

<210> SEQ ID NO 76
<211> LENGTH: 38
<212> TYPE: DNA
<213> ORGANISM: Artificial Sequence
<220> FEATURE:

<223> OTHER INFORMATION: target for Eubacterial16s ribosomal RNA gene
      region I

<400> SEQUENCE: 76
tcggtacaga gggtcgccaa accgcgaggt ggagctaa                                   38

<210> SEQ ID NO 77
<211> LENGTH: 38
<212> TYPE: DNA
<213> ORGANISM: Artificial Sequence
<220> FEATURE:
<223> OTHER INFORMATION: target for Eubacterial16s ribosomal RNA gene
      region II

<400> SEQUENCE: 77
ggatgaaagg agcttgctcc tggattcagc ggcggacg                                   38

<210> SEQ ID NO 78
<211> LENGTH: 24
<212> TYPE: DNA
<213> ORGANISM: Artificial Sequence
<220> FEATURE:
<223> OTHER INFORMATION: target for Gram +ve bacterial specific portion
      of 16a ribosomal RNA gene

<400> SEQUENCE: 78
gacctgggct acacacgtgc taca                                                  24

<210> SEQ ID NO 79
<211> LENGTH: 42
<212> TYPE: DNA
<213> ORGANISM: Artificial Sequence
<220> FEATURE:
<223> OTHER INFORMATION: target for Mycobacterium tuberculosis MPB 64
      gene

<400> SEQUENCE: 79
ctgggttggg ccggctgctt cgggcagcaa ctcccccggg tt                              42

<210> SEQ ID NO 80
<211> LENGTH: 26
<212> TYPE: DNA
<213> ORGANISM: Artificial Sequence
<220> FEATURE:
<223> OTHER INFORMATION: target for Mycobacterium fortuitum 16s - 23s
      RNA gene

<400> SEQUENCE: 80
ggctttgaga caacaggccc gtgccc                                                26

<210> SEQ ID NO 81
<211> LENGTH: 23
<212> TYPE: DNA
<213> ORGANISM: Artificial Sequence
<220> FEATURE:
<223> OTHER INFORMATION: target for Mycobacterium chelonae 16s - 23s
      RNA gene

<400> SEQUENCE: 81
tttataaatc ctgtccaccc cgt                                                   23

<210> SEQ ID NO 82
<211> LENGTH: 27
<212> TYPE: DNA
<213> ORGANISM: Artificial Sequence
<220> FEATURE:
<223> OTHER INFORMATION: target for Toxoplasma gondii B1 gene -continued

```
<400> SEQUENCE: 82
aaattcatga gtatctgtgc aactttg                                      27

<210> SEQ ID NO 83
<211> LENGTH: 32
<212> TYPE: DNA
<213> ORGANISM: Artificial Sequence
<220> FEATURE:
<223> OTHER INFORMATION: target for Chlamydia trachomatis polymorphic
      protein II

<400> SEQUENCE: 83
atgatgcttt atcaaatgac aagcttagat cc                                32

<210> SEQ ID NO 84
<211> LENGTH: 25
<212> TYPE: DNA
<213> ORGANISM: Artificial Sequence
<220> FEATURE:
<223> OTHER INFORMATION: target for fungal specific portion of 28a
      ribosomal RNA gene

<400> SEQUENCE: 84
gtaagtcaag gatgctggca taatg                                        25

<210> SEQ ID NO 85
<211> LENGTH: 26
<212> TYPE: DNA
<213> ORGANISM: Artificial Sequence
<220> FEATURE:
<223> OTHER INFORMATION: target for Propionibacterium acnes specific
      portion of 16s-23 ribosomal RNA gene

<400> SEQUENCE: 85
gcttcagcgc cgtcagcgag gataac                                       26

<210> SEQ ID NO 86
<211> LENGTH: 30
<212> TYPE: DNA
<213> ORGANISM: Artificial Sequence
<220> FEATURE:
<223> OTHER INFORMATION: target for Gram -ve bacterial specific portion
      of gyr B gene

<400> SEQUENCE: 86
aacacctaca aggtgtccgg cggcttgcac                                   30

<210> SEQ ID NO 87
<211> LENGTH: 31
<212> TYPE: DNA
<213> ORGANISM: Artificial Sequence
<220> FEATURE:
<223> OTHER INFORMATION: target for Gram -ve bacterial aconitate
      hydratase gene

<400> SEQUENCE: 87
cgaggcaggc gaggtccttc agttcgtcgc g                                 31

<210> SEQ ID NO 88
<211> LENGTH: 27
<212> TYPE: DNA
<213> ORGANISM: Artificial Sequence
<220> FEATURE:
<223> OTHER INFORMATION: target for Gram -ve bacterial ribonuclease 1
      gene
```

```
<400> SEQUENCE: 88
atcagcctgg ccggccgtta cctggtg                                              27
```